(12) United States Patent
Guarin et al.

(10) Patent No.: US 11,039,769 B2
(45) Date of Patent: Jun. 22, 2021

(54) ELECTROMAGNETIC WAVE SENSOR FOR DETERMINING A HYDRATION STATUS OF A BODY TISSUE IN VIVO

(71) Applicant: Infineon Technologies AG, Neubiberg (DE)

(72) Inventors: Gustavo Adolfo Guarin, Nuremberg (DE); Maximilian Hofmann, Nuremberg (DE); Dietmar Kissinger, Erlangen (DE); Herbert Roedig, Riemerling (DE); Tanja Seiderer, Unterhaching (DE)

(73) Assignee: Infineon Technologies AG

( * ) Notice: Subject to any disclaimer, the term of this patent is extended or adjusted under 35 U.S.C. 154(b) by 256 days.

(21) Appl. No.: 15/773,776

(22) PCT Filed: Nov. 4, 2016

(86) PCT No.: PCT/EP2016/076696
§ 371 (c)(1),
(2) Date: May 4, 2018

(87) PCT Pub. No.: WO2017/077052
PCT Pub. Date: May 11, 2017

(65) Prior Publication Data
US 2018/0325431 A1 Nov. 15, 2018

(30) Foreign Application Priority Data
Nov. 6, 2015 (DE) .......................... 102015119180.6

(51) Int. Cl.
*A61B 5/1455* (2006.01)
*A61B 5/1495* (2006.01)
(Continued)

(52) U.S. Cl.
CPC .......... *A61B 5/1495* (2013.01); *A61B 5/0507* (2013.01); *A61B 5/0537* (2013.01);
(Continued)

(58) Field of Classification Search
None
See application file for complete search history.

(56) References Cited

U.S. PATENT DOCUMENTS

2005/0107718 A1   5/2005   Hashimshony
2007/0197888 A1   8/2007   Axelrod et al.
(Continued)

FOREIGN PATENT DOCUMENTS

DE   10 2012 203 880 A1   9/2013
WO       2010118537 A1   10/2010
(Continued)

OTHER PUBLICATIONS

Kraszewski, A. W., "Microwave aquametry—Needs and perspectives", IEEE—Transactions on microwave theory and techniques, vol. 39, Nr. 5 (May 5, 1991), pp. 828-835.

*Primary Examiner* — Eric F Winakur
*Assistant Examiner* — Marjan Fardanesh
(74) *Attorney, Agent, or Firm* — Design IP

(57) ABSTRACT

An electromagnetic wave sensor for determining a hydration status of a body tissue in vivo includes an electromagnetic wave transmitter, a waveguide, and an electromagnetic wave receiver. The electromagnetic wave transmitter is configured to emit an electromagnetic wave signal in a frequency range between 1 Hz and 1 THz. The waveguide is coupled to the electromagnetic wave transmitter. The waveguide is adapted to be arranged next to the body tissue such that a fringe field of the electromagnetic wave signal guided by the waveguide penetrates the body tissue. The electromagnetic wave receiver is coupled to the waveguide. The electromagnetic (Continued)

wave receiver is configured to receive the electromagnetic wave signal modified by the body tissue in dependence of a hydration status of the body tissue.

16 Claims, 22 Drawing Sheets

(51) Int. Cl.
    *A61B 5/0507*     (2021.01)
    *A61B 5/00*     (2006.01)
    *A61B 5/145*     (2006.01)
    *A61B 5/0537*     (2021.01)

(52) U.S. Cl.
    CPC ........ *A61B 5/14532* (2013.01); *A61B 5/4869* (2013.01); *A61B 5/4875* (2013.01); *A61B 5/6833* (2013.01); *A61B 5/681* (2013.01); *A61B 5/6803* (2013.01); *A61B 2560/0214* (2013.01)

(56) References Cited

U.S. PATENT DOCUMENTS

| | | |
|---|---|---|
| 2008/0021343 A1 | 1/2008 | Hashimshony et al. |
| 2011/0160554 A1 | 6/2011 | Megej et al. |
| 2012/0220835 A1 | 8/2012 | Chung |
| 2017/0164878 A1* | 6/2017 | Connor .................. A61B 5/053 |

FOREIGN PATENT DOCUMENTS

| | | |
|---|---|---|
| WO | 2010149984 A1 | 12/2010 |
| WO | 2016005050 A1 | 1/2016 |

* cited by examiner

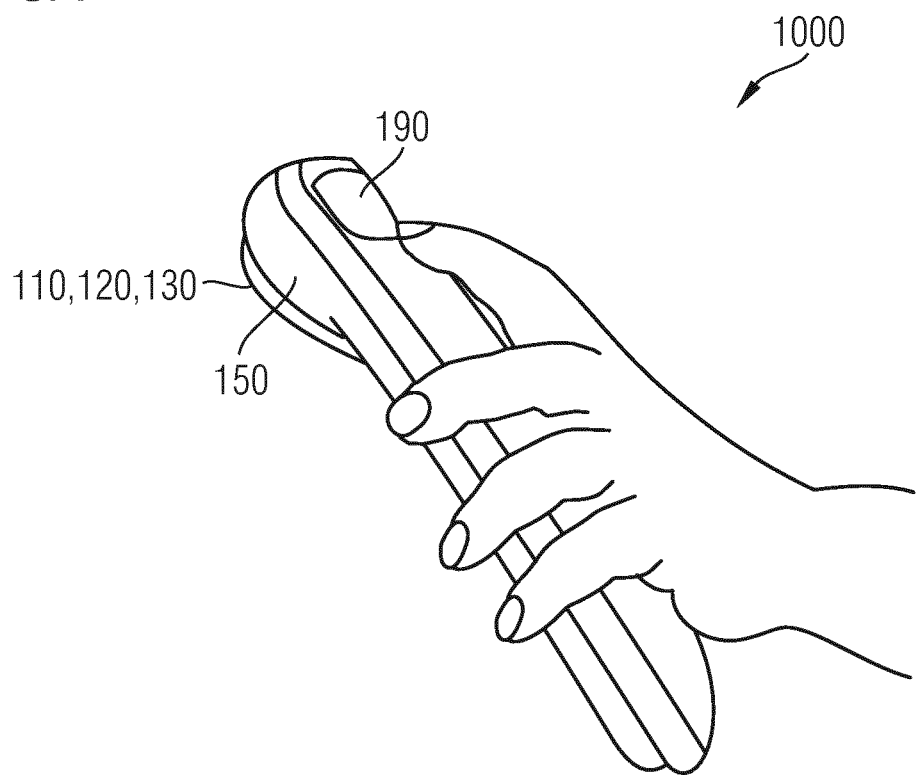

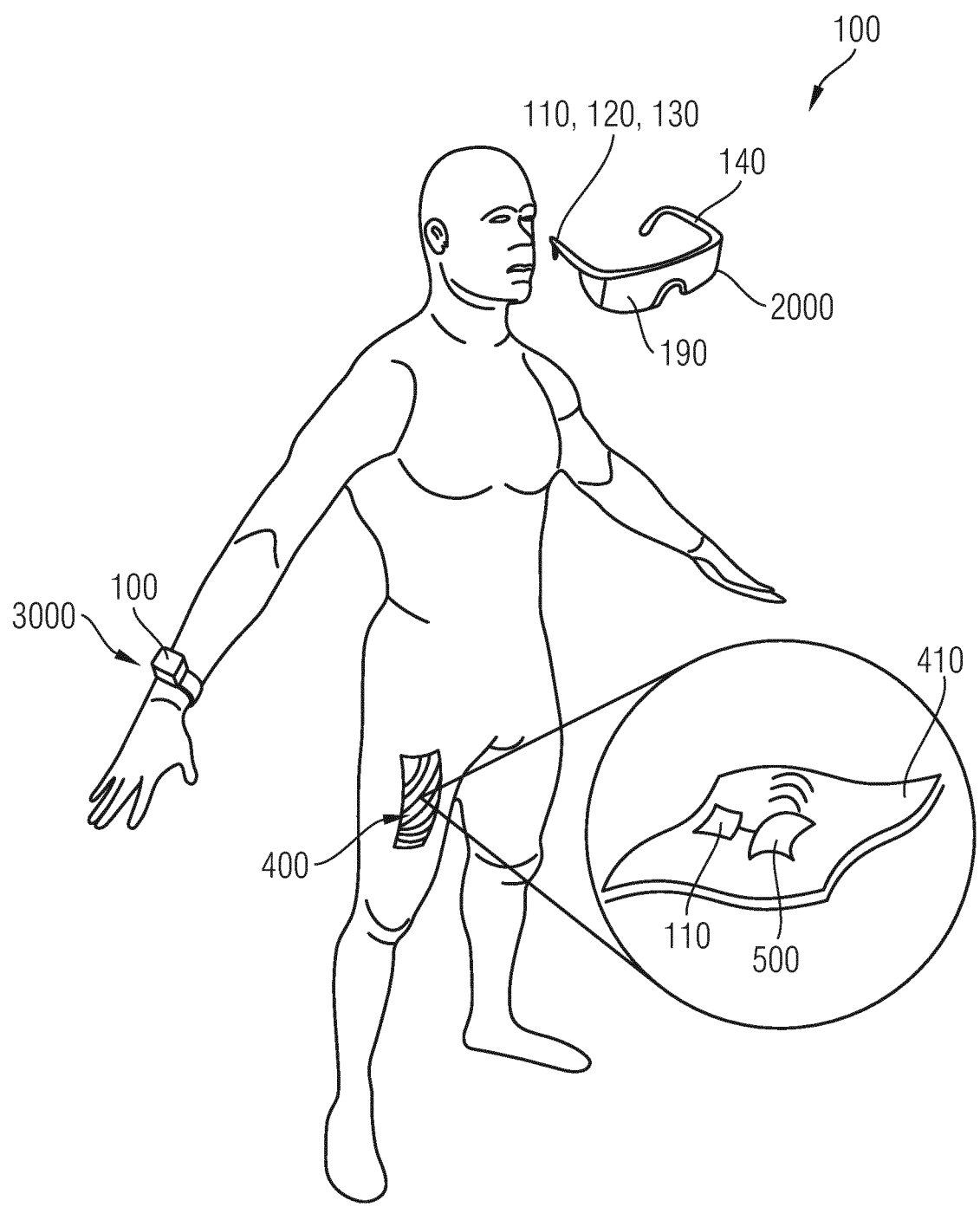

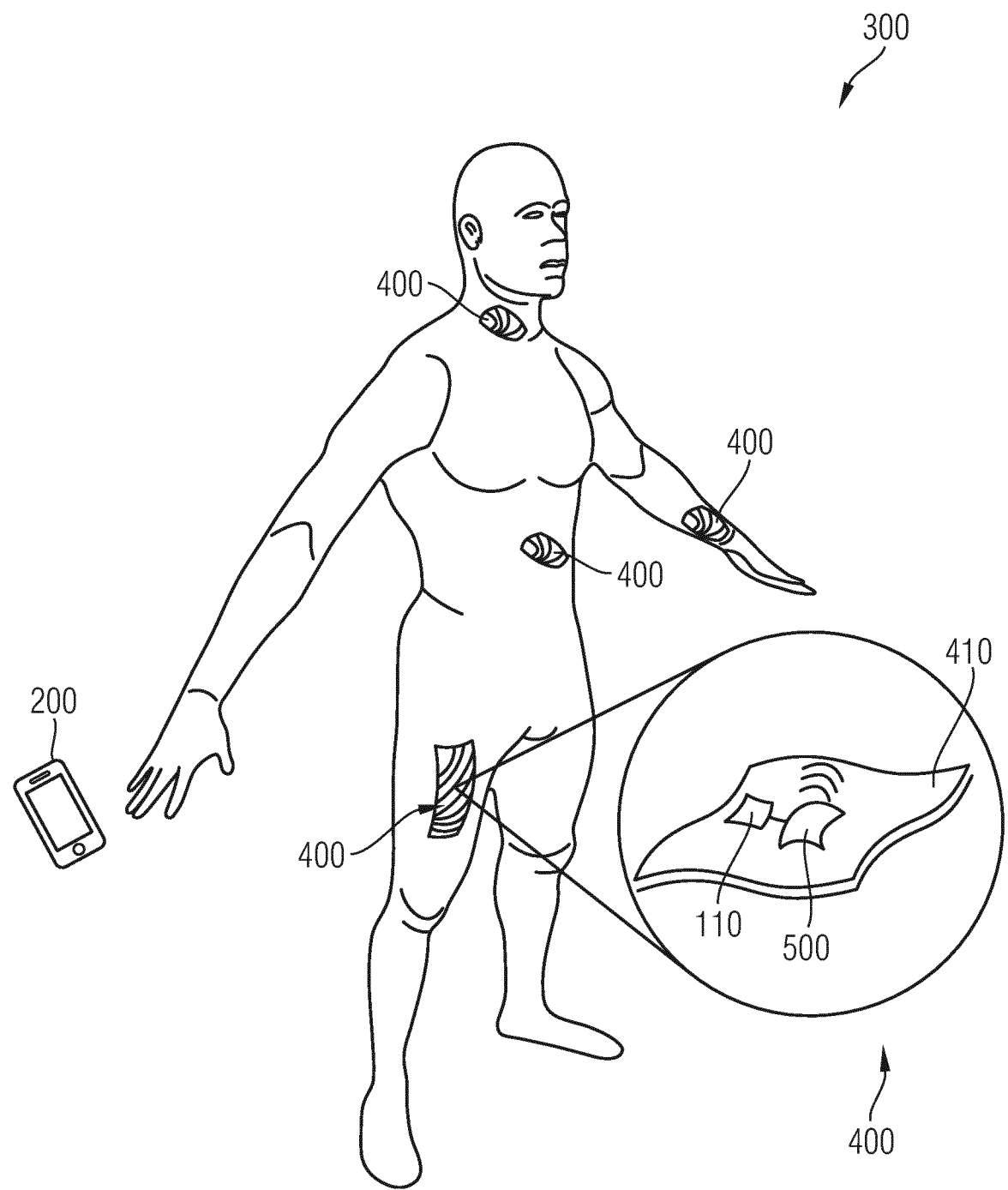

ELECTROMAGNETIC WAVE SENSOR FOR DETERMINING A HYDRATION STATUS OF A BODY TISSUE IN VIVO

CROSS REFERENCE TO RELATED APPLICATIONS

This application is the U.S. National Stage, under 35 U.S.C. § 371, of International Application No. PCT/EP2016/076696 filed Nov. 4, 2016, which claims the benefit of German Patent Application No. 10 2015 119 180.6 filed Nov. 6, 2015, the content of which is hereby incorporated by reference herein.

BACKGROUND

Proper hydration is one of the most important factors in maintaining homeostasis within the body as well as sustaining optimal physiological and psychological performance. Appropriate daily hydration with water is necessary for maintaining energy levels, regulating body temperature, digestion and absorption of nutrients, elimination of toxins and waste, joint lubrication, reproduction and neural conductivity. Interestingly, regardless of the reported importance of proper hydration in maintaining good health, epidemiological data appears to indicate that a majority of individuals are mildly dehydrated due to not drinking enough water on a daily basis. Besides, information about the hydration level is more relevant for some groups of population like elder people, athletes, persons that suffers from chronic kidney disease and infants.

On the other side, several diseases are associated with altered fluid balance in the body (including human immunodeficiency virus, cancer, infections septic shock, kidney failure and multiple sclerosis).

In spite of the fact, that the monitoring of the hydration level is very important in the daily life, a dependable method for accurately monitoring changes in hydration status that has the low cost, convenience and practicality necessary for widespread use currently does not exist. Methods that are available are either indirect and unreliable, or dependent on blood and urine tests that are invasive, complex and frequently costly.

It is an object of the present invention to provide a device for determining a hydration status of a body tissue in vivo having an improved reliability and precision.

SUMMARY

This object is solved by the subject-matter of the independent claims. Further advantageous embodiments and refinements are defined in the respective sub-claims.

According to an embodiment of an electromagnetic wave sensor for determining a hydration status of a body tissue in vivo, the electromagnetic wave sensor includes an electromagnetic wave transmitter unit, a waveguide unit, and an electromagnetic wave receiver unit. The electromagnetic wave transmitter unit is configured to emit an electromagnetic wave signal in a frequency range between 1 Hz and 1 THz. The waveguide unit is coupled to the electromagnetic wave transmitter unit. The waveguide unit is adapted to be arranged next to the body tissue such that a fringe field of the electromagnetic wave signal guided by the waveguide unit penetrates the body tissue. The electromagnetic wave receiver unit is coupled to the waveguide unit. The electromagnetic wave receiver unit is configured to receive the electromagnetic wave signal modified by the body tissue in dependence of the hydration status of the body tissue.

According to an embodiment of a system for determining a hydration status of a body tissue in vivo, the system includes the electromagnetic wave sensor and an external device. The electromagnetic wave sensor includes a communication unit adapted to transmit data related to the electromagnetic wave signal modified by the body tissue in dependence of the hydration status of the body tissue to an external device. The external device is configured to receive data from the electromagnetic wave sensor related to the electromagnetic wave signal modified by the body tissue in dependence of the hydration status of the body tissue.

According to an embodiment of a skin patch, the skin patch includes a skin patch body adapted to be adhered to a skin of a body. The skin patch further includes a waveguide unit adapted to be coupled to an electromagnetic wave transmitter unit and an electromagnetic wave receiver unit. The waveguide unit is arranged on the skin patch body such that a fringe field of the electromagnetic wave signal can penetrate the body tissue when the skin patch body is adhered to the skin of the body.

Those skilled in the art will recognize additional features and advantages upon reading the following detailed description and on viewing the accompanying drawings.

BRIEF DESCRIPTION OF THE DRAWINGS

The accompanying drawings are included to provide a further understanding of the invention and are incorporated in and constitute a part of this specification. The drawings illustrate the embodiments of the present invention and together with the description serve to explain principles of the invention. Other embodiments of the invention and intended advantages will be readily appreciated as they become better understood by reference to the following detailed description. The elements of the drawings are not necessarily to scale relative to each other. Like reference numerals designate corresponding similar parts. The features of the various illustrated embodiments can be combined unless they exclude each other.

FIG. 3A is a schematic perspective view of a handheld device comprising the electromagnetic wave sensor according to one or more embodiments.

FIG. 3B is a schematic perspective view of a human body wearing electromagnetic wave sensors according to one or more embodiments.

FIG. 3C is a schematic perspective view of a system for determining a hydration status of a body tissue in vivo attached to a human body according to one or more embodiments.

FIG. 5I is a diagram illustrating the penetrating depth of a microwave signal for different tissues as a function of the frequency according to one or more embodiments.

DETAILED DESCRIPTION

In the following detailed description, reference is made to the accompanying drawings, which form a part hereof, and in which are shown by way of illustrations specific embodiments in which embodiments may be practiced. It is to be understood that other embodiments may be utilized and structural or logical changes may be made without departing from the scope of the embodiments. For example, features illustrated or described for one embodiment can be used on or in conjunction with other embodiments to yield yet a further embodiment. It is intended that the embodiments include such modifications and variations. The examples are described using specific language which should not be construed as limiting the scope of the appending claims. The drawings are not scaled and are for illustrative purposes only. For clarity, the same elements have been designated by corresponding references in the different drawings if not stated otherwise.

The terms "having", "containing", "including", "comprising" and the like are open and the terms indicate the presence of stated structures, elements or features but not preclude additional elements or features. The articles "a", "an" and "the" are intended to include the plural as well as the singular, unless the context clearly indicates otherwise.

The term "electrically connected" describes a permanent low-ohmic connection between electrically connected elements, for example a direct contact between the concerned elements or a low-ohmic connection via a metal and/or highly doped semiconductor. The term "electrically coupled" includes that one or more intervening element(s) adapted for signal transmission may be provided between the electrically coupled elements, for example resistors, resistive elements or elements that are controllable to temporarily provide a low-ohmic connection in a first state and a high-ohmic electric decoupling in a second state.

Figure 1A:
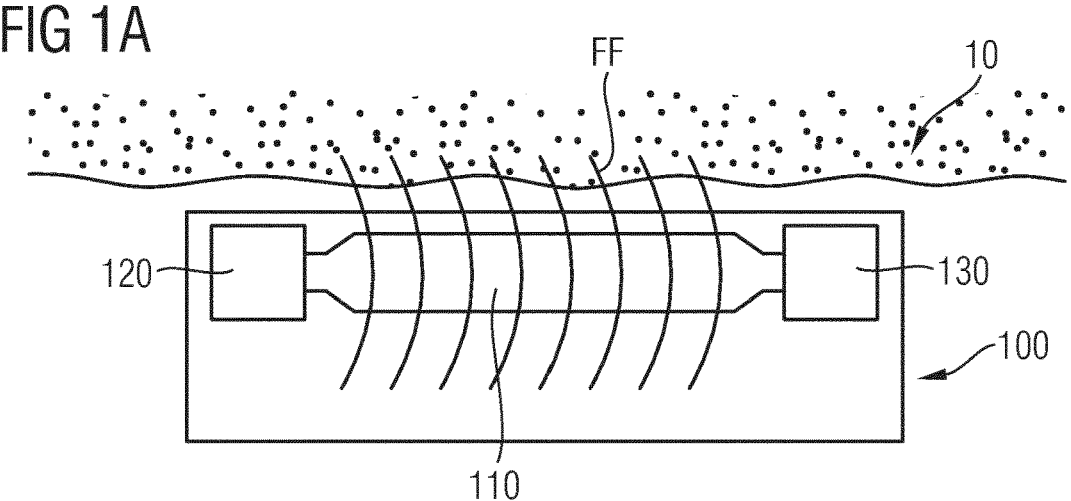
FIG. 1A is a schematic block diagram of an electromagnetic wave sensor according to one or more embodiments.

FIG. 1A is a schematic block diagram of an electromagnetic wave sensor 100 for determining a hydration status of a body tissue 10 in vivo according to an embodiment. As shown in FIG. 1A, the electromagnetic wave sensor 100 comprises an electromagnetic wave transmitter unit 120, a waveguide unit 110, and an electromagnetic wave receiver unit 130. The electromagnetic wave transmitter unit 120 is configured to emit an electromagnetic wave signal in a frequency range between 1 Hz and 1 THz. The waveguide unit 110 is coupled to the electromagnetic wave transmitter unit 120. The waveguide unit 110 is adapted to be arranged next to the body tissue 10 such that a fringe field FF of the electromagnetic wave signal guided by the waveguide unit 110 penetrates the body tissue 10. The electromagnetic wave receiver unit 130 is coupled to the waveguide unit 110. The electromagnetic wave receiver unit 130 is configured to receive the electromagnetic wave signal modified by the body tissue 10 in dependence of the hydration status of the body tissue 10.

The body tissue 10 shall be understood as that part of the tissue of a human body or animal body, which is penetrated by the electromagnetic wave signal emitted by the electromagnetic wave transmitter unit 120 and which has an influence on the electromagnetic wave signal in such a way that the electromagnetic wave signal is modified. A modification of the electromagnetic wave signal may be an attenuation or phase change of the electromagnetic wave signal in dependence of the electromagnetic wave frequency, for example. The electromagnetic wave signal modified by the body tissue 10 is then received by the electromagnetic wave receiver unit 140 after transmission or reflection. By comparing the modified electromagnetic wave signal with the emitted electromagnetic wave signal, a transfer function being the ratio of the modified electromagnetic wave signal and the emitted electromagnetic wave signal can be determined, which allows a measurement of the hydration status of the body tissue 10.

Figure 1B:
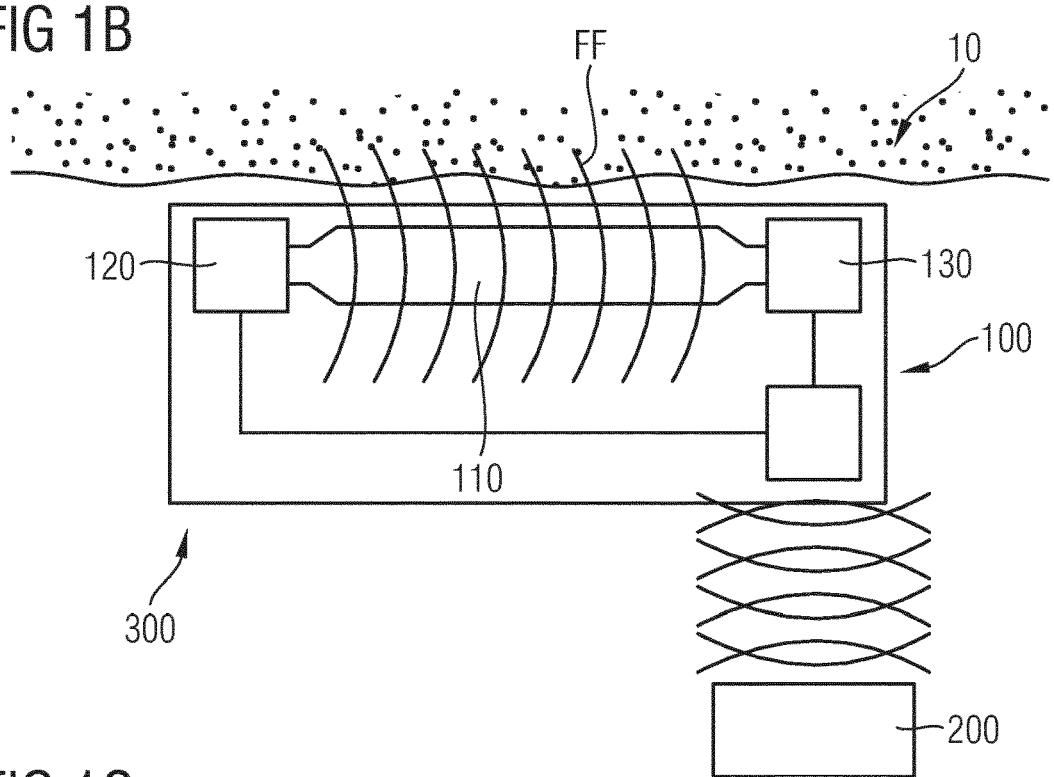
FIG. 1B is a schematic block diagram of a system for determining a hydration status of a body tissue in vivo according to one or more embodiments.

FIG. 1B is a schematic block diagram of a system 300 for determining a hydration status of a body tissue 10 in vivo according to an embodiment. As can be seen from FIG. 1B, the system 300 comprises the electromagnetic wave sensor 100, which further comprises a communication unit 140 adapted to transmit data related to the electromagnetic wave signal modified by the body tissue 10 in dependence of the hydration status of the body tissue 10 to an external device 200. The system 300 further comprises the external device 200, which is configured to receive data from the electromagnetic wave sensor 100 related to the electromagnetic wave signal modified by the body tissue 10 in dependence of the hydration status of the body tissue 10.

According to an embodiment, the external device 200 may be configured to transmit radio frequency energy in a frequency range between 400 MHz and 1 GHz powering the electromagnetic wave sensor 100. In another embodiment, the external device 200 may be configured to power the electromagnetic wave sensor 100 by inductive magnetic coupling in a frequency range between 100 kHz and 20 MHz. The external device 200 is further configured to receive radio frequency signals from the electromagnetic wave sensor 100 related to the electromagnetic wave signal modified by the body tissue 10.

Figure 1C:
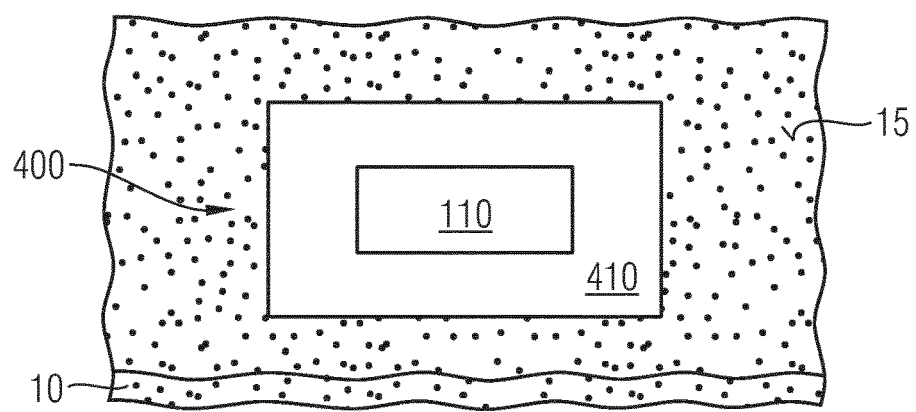
FIG. 1C is a schematic block diagram of a skin patch according to one or more embodiments.

FIG. 1C is a schematic block diagram of a skin patch 400 according to an embodiment. As can be seen from FIG. 1C, the skin patch 400 comprises a skin patch body 410, which is adapted to be adhered to a skin 15 of a body. The skin patch 400 further comprises a waveguide unit 110, which is adapted to be coupled to an electromagnetic wave transmitter unit 120 and an electromagnetic wave receiver unit 130. The waveguide unit 110 is arranged on the skin patch body 410 such that a fringe field FF of the electromagnetic wave signal can penetrate a body tissue 10 when the skin patch body 410 is adhered to the skin 15 of the body.

FIG. 2A to 2D are schematic diagrams illustrating various employments of the electromagnetic wave sensor 100, the system 300 and the skin patch 400 according to different embodiments. FIG. 3A to FIG. 3D are schematic perspective views of an electromagnetic wave sensor 100, a system 300 for determining a hydration status of a body tissue 10 in vivo and a skin patch 400 embodied as different products according to different embodiments.

Figure 2A:
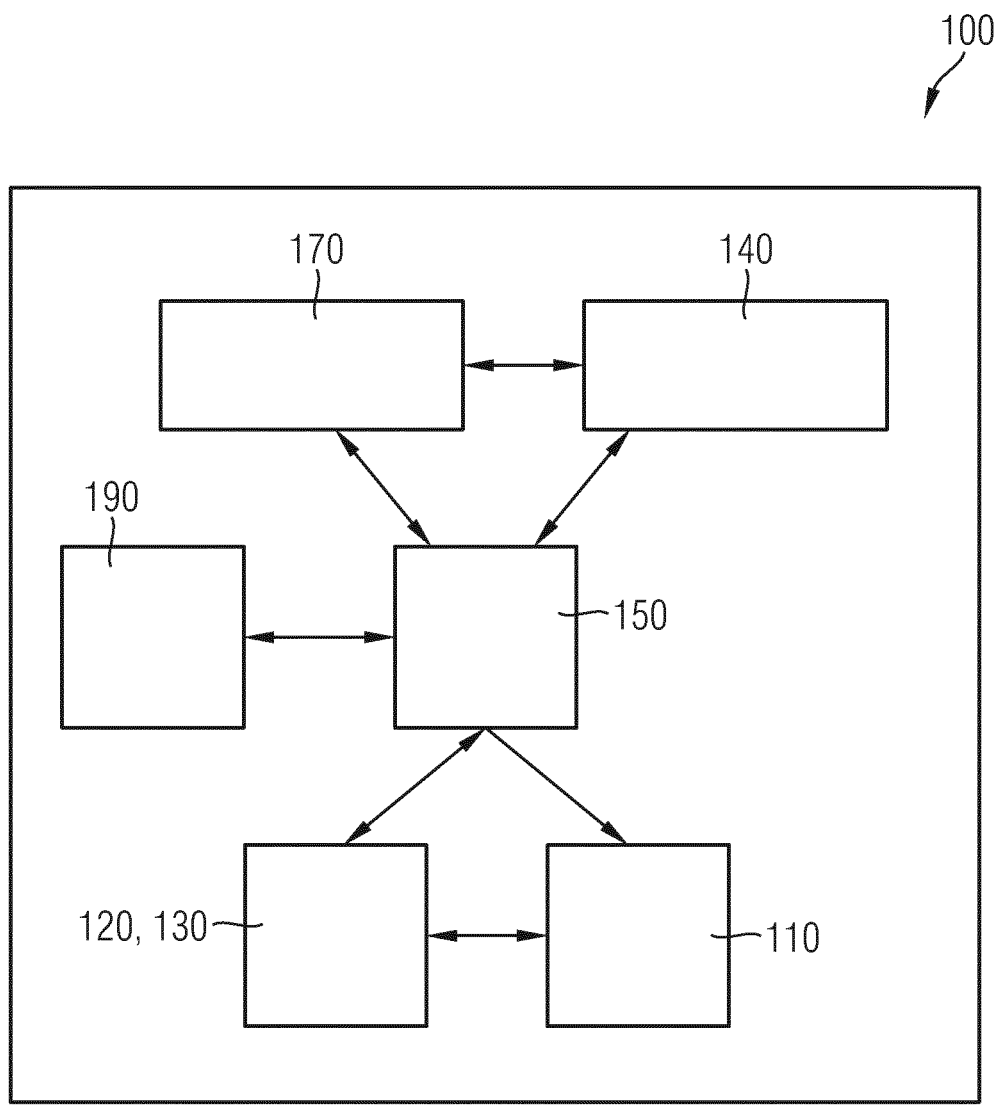
FIGS. 2A and 2B are schematic block diagrams of an electromagnetic wave sensor embodied in a single device according to different embodiments.

As can be seen from FIG. 2A, the electromagnetic wave sensor 100 may comprise the waveguide unit 110, wherein one or multiple elements may couple the electromagnetic signal to the body tissue 10. The waveguide unit 110 can be in the form of an open waveguide, a leaky waveguide or a planar waveguide. The propagation constant of the waveguide unit 110 changes as a function of the water content and electrolyte content in the body tissue 10.

The waveguide unit 110 is coupled to the electromagnetic wave transmitter unit 120 and the electromagnetic wave receiver unit 130. According to an embodiment, the electromagnetic wave transmitter unit 120 is adapted to generate an electromagnetic signal between DC or 1 Hz and 1 THz in order to excite the waveguide unit 110. According to another embodiment, the electromagnetic wave transmitter unit 120 is adapted to generate an electromagnetic signal between DC or 1 Hz and 300 GHz in order to excite the waveguide unit 110. According to another embodiment, the electromagnetic wave transmitter unit 120 is adapted to generate an electromagnetic signal between DC or 1 Hz and 30 GHz in order to excite the waveguide unit 110. According to another embodiment, the electromagnetic wave transmitter unit 120 is adapted to generate an electromagnetic signal between DC or 1 Hz and 10 GHz in order to excite the waveguide unit 110. According to another embodiment, the electromagnetic wave transmitter unit 120 is adapted to generate an electromagnetic signal between 100 MHz and 10 GHz in order to excite the waveguide unit 110. The generated signal can be a frequency modulated signal or a pseudo random binary sequence (PRBS).

The electromagnetic wave receiver unit 130 acquires the reflected and/or the transmitted signal of the waveguide unit 110 and digitalizes these signals in order to be processed by a processor unit 150. The processor unit 150 is adapted to determine the hydration status of the body tissue 10 from the electromagnetic wave signal modified by the body tissue 10 in dependence of the hydration status of the body tissue 10.

According to an embodiment, the electromagnetic wave receiver unit 130 may be adapted to receive the electromagnetic wave signal transmitted by the waveguide unit 110. According to another embodiment, the electromagnetic wave receiver unit 130 may be adapted to receive the electromagnetic wave signal reflected in the waveguide unit 110. According to still another embodiment, the electromagnetic wave receiver unit 130 may be adapted to both receive the electromagnetic wave signal transmitted by the waveguide unit 110 or reflected in the waveguide unit 110. The electromagnetic wave transmitter unit 120 may be configured to emit electromagnetic wave signals in a frequency range between 1 GHz and 100 GHz. The processor unit 150 may be adapted to process the emitted signal and the received signals from the waveguide unit 110 in order to determine the propagation constant or transfer function of the waveguide unit 110 as a function of the frequency. With the propagation constant of the waveguide unit 110, the values of water content and electrolyte content of the body tissue 10 may be calculated also on the processor unit 150. The hydration status of the body tissue 10 in vivo should be understood as a water content and electrolyte content of the body tissue 10 of a living body.

As can be further seen from FIG. 2A, the electromagnetic wave sensor 100 may comprise a communication unit 140, which is adapted to transmit data related to the electromagnetic wave signal modified by the body tissue 10 in dependence of the hydration status of the body tissue 10 to an external device 200. Thus, the communication unit 140 may be adapted to transmit sensor information to other devices or to a user interface. This can be done in form of a wireless communication or with wire.

The electromagnetic wave sensor 100 may further comprise a graphical user interface 190, which is adapted to indicate the hydration status to a user. The graphical user interface 190 may display the hydration information in form of raw data (time series), in form of a traffic light system or in form of alphanumerical data. With a traffic light system, three colours will indicate to the patient or user the hydration level. Green indicates appropriate hydrated, orange indicates in process of dehydration and red indicates a dangerous level of dehydration.

In addition, the electromagnetic wave sensor may further comprise an energy storage unit 170 for supplying energy to the electromagnetic wave sensor 100. Herein, the electromagnetic wave sensor 100 may further comprise an energy harvesting unit 180, which is configured to harvest energy from an external power source, as will be described in all detail below.

Figure 2B:
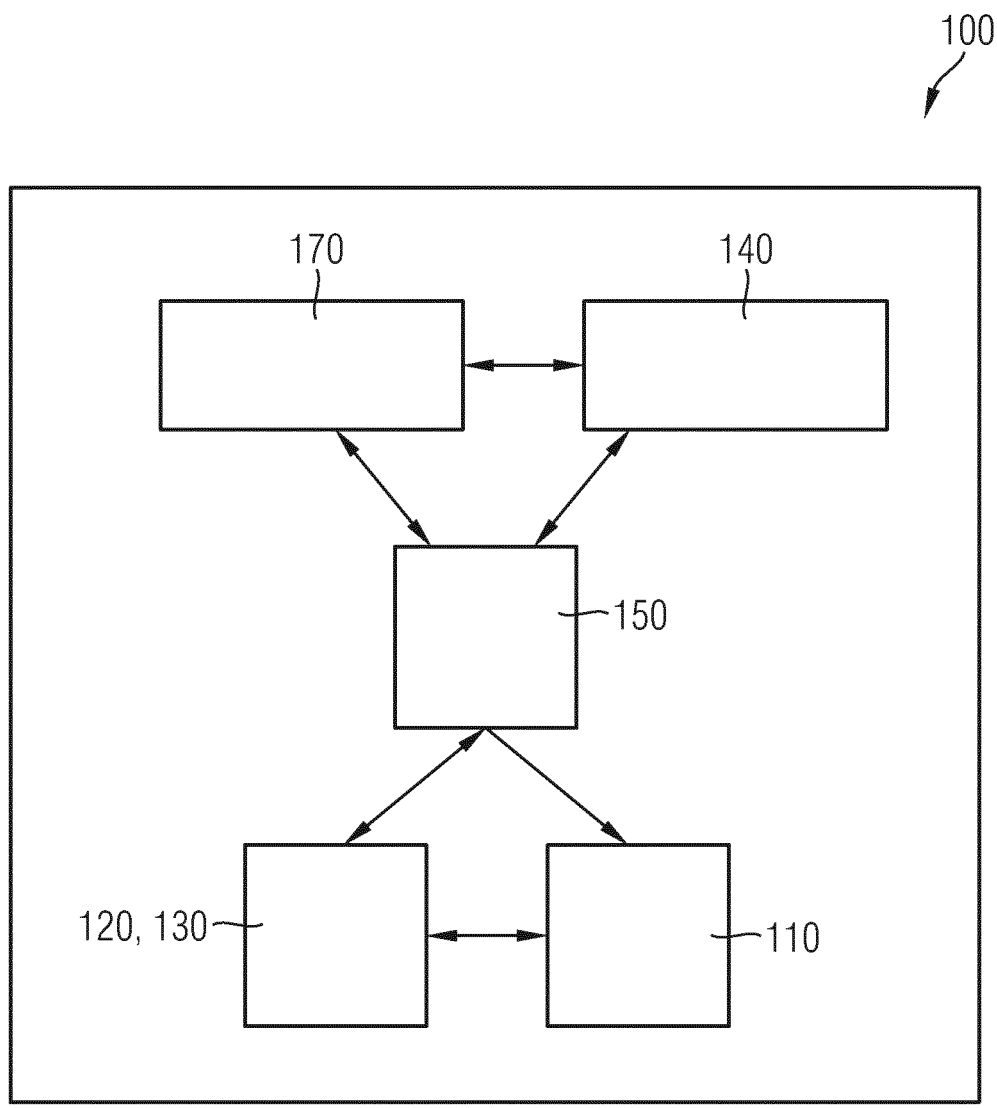

According to another embodiment as shown in FIG. 2B, the electromagnetic wave sensor 100 may also transmit the sensor information via the communication unit 140 to an external graphical user interface or a data recording station.

An example of a product implementation of the electromagnetic wave sensor 100 of FIG. 2A is shown in FIG. 3A. Herein, the electromagnetic wave sensor 100 is integrated in a handheld device 1000. The electromagnetic wave transmitter unit 120, the waveguide unit 110 and the electromagnetic wave receiver unit 130 may be integrated in a distal part of the handheld device 1000. The waveguide unit 110 may be arranged next to the body tissue 10 such that a fringe field FF of the electromagnetic wave signal guided by the waveguide unit 110 penetrates the body tissue 10 when the handheld device 1000 is pressed against the skin of a user. Within the handheld device 1000, the processor unit 150 is integrated to determine the hydration status of the body tissue 10 from the electromagnetic wave signal modified by the body tissue 10 in dependence of the hydration status of the body tissue 10, which may be then indicated by the graphical user interface 190 to a user.

A further product implementation of an electromagnetic wave sensor 100 of FIG. 2A can be seen in FIG. 3B. Herein, the electromagnetic wave sensor 100 may be integrated in glasses 2000. The waveguide unit 110, the electromagnetic wave transmitter unit 120 and the electromagnetic wave receiver unit 130 may be integrated in the ear piece or the temple arm of the glasses 2000 such that the waveguide unit 110 is arranged next to the body tissue 10 of a human body wearing the glasses 2000. In operation of the electromagnetic wave sensor 100, a fringe field of the electromagnetic wave signal guided by the waveguide unit 110 penetrates the body tissue 10. The electromagnetic wave sensor 100 integrated in the glasses 2000 may further comprise the graphical user interface 190, which might be embodied as a head-up display integrated in the viewing field of the glasses 2000. The electromagnetic wave sensor 100 integrated in the glasses 2000 may further comprise the communication unit 140 to transfer sensor data from the waveguide unit 110 to an external device 200.

According to another embodiment of the electromagnetic wave sensor 100, the electromagnetic wave sensor 100 may be integrated in a wrist watch 3000. As can be seen from FIGS. 3B and 3D, the wrist watch 3000 may have the waveguide unit 110, the electromagnetic wave transmitter unit 120 and the electromagnetic wave receiver unit 130 integrated in the wristband of the wrist watch 3000. The sensor data of the electromagnetic wave receiver unit 130 and the electromagnetic wave transmitter unit 120 may be processed by a processor unit 150 integrated in the wrist watch 3000. The wrist watch 3000 may further comprise the graphical user interface 190 to indicate the hydration status of the body tissue 10 to a user. The above embodiment should not be understood as limited to a wrist watch 3000, it is, however, also possible to integrate the electromagnetic wave sensor 100 in a mobile device having a wrist band, an arm band or a leg band such that the waveguide unit 110 is adapted to be arranged next to a body tissue such that a fringe field of the electromagnetic wave signal guided by the waveguide unit 110 penetrates the body tissue 10.

Figure 2C:
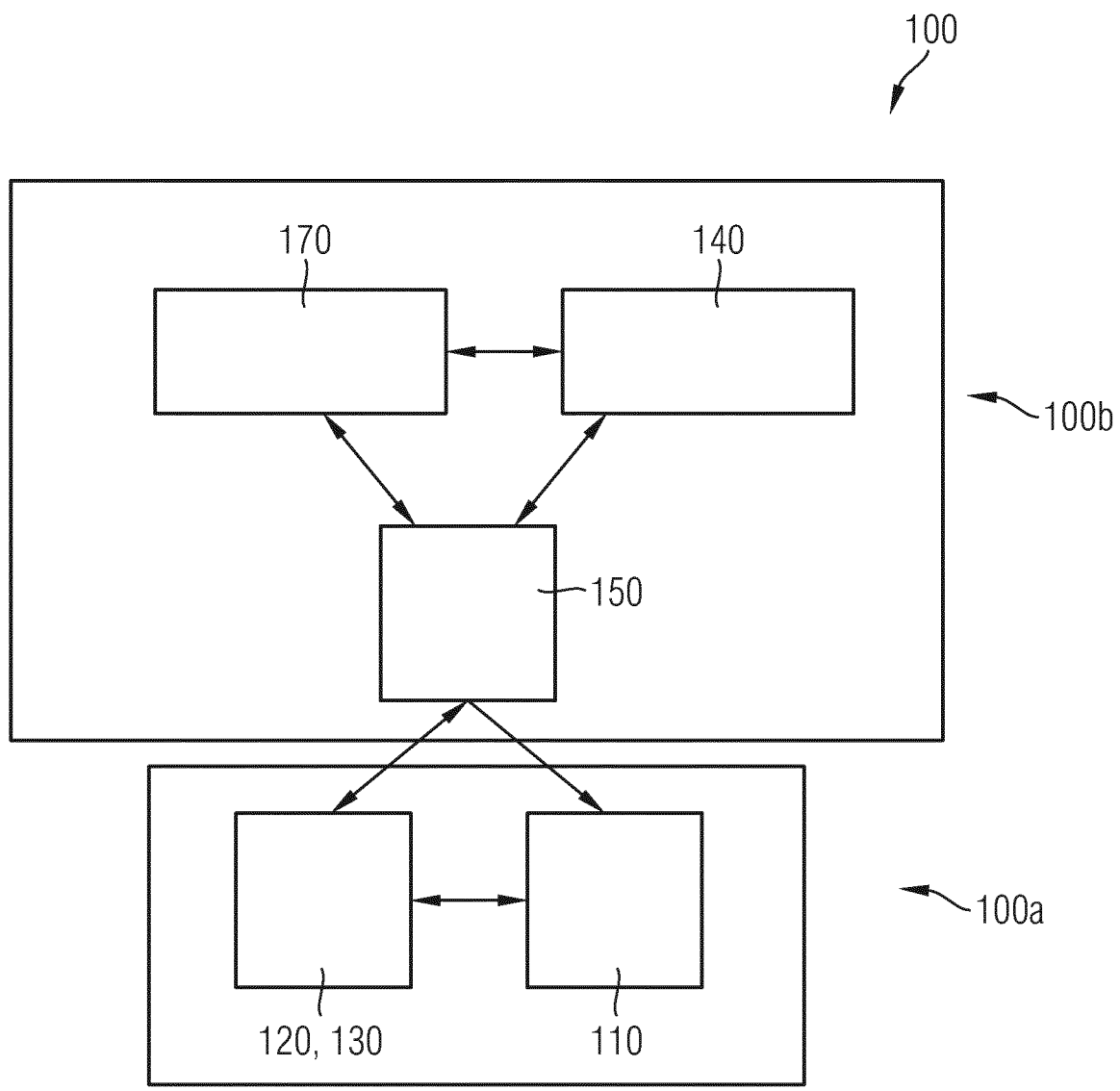
FIGS. 2C and 2D are schematic block diagrams of an electromagnetic wave sensor including a disposable part and a non-disposable part according to different embodiments.
Figure 2D:
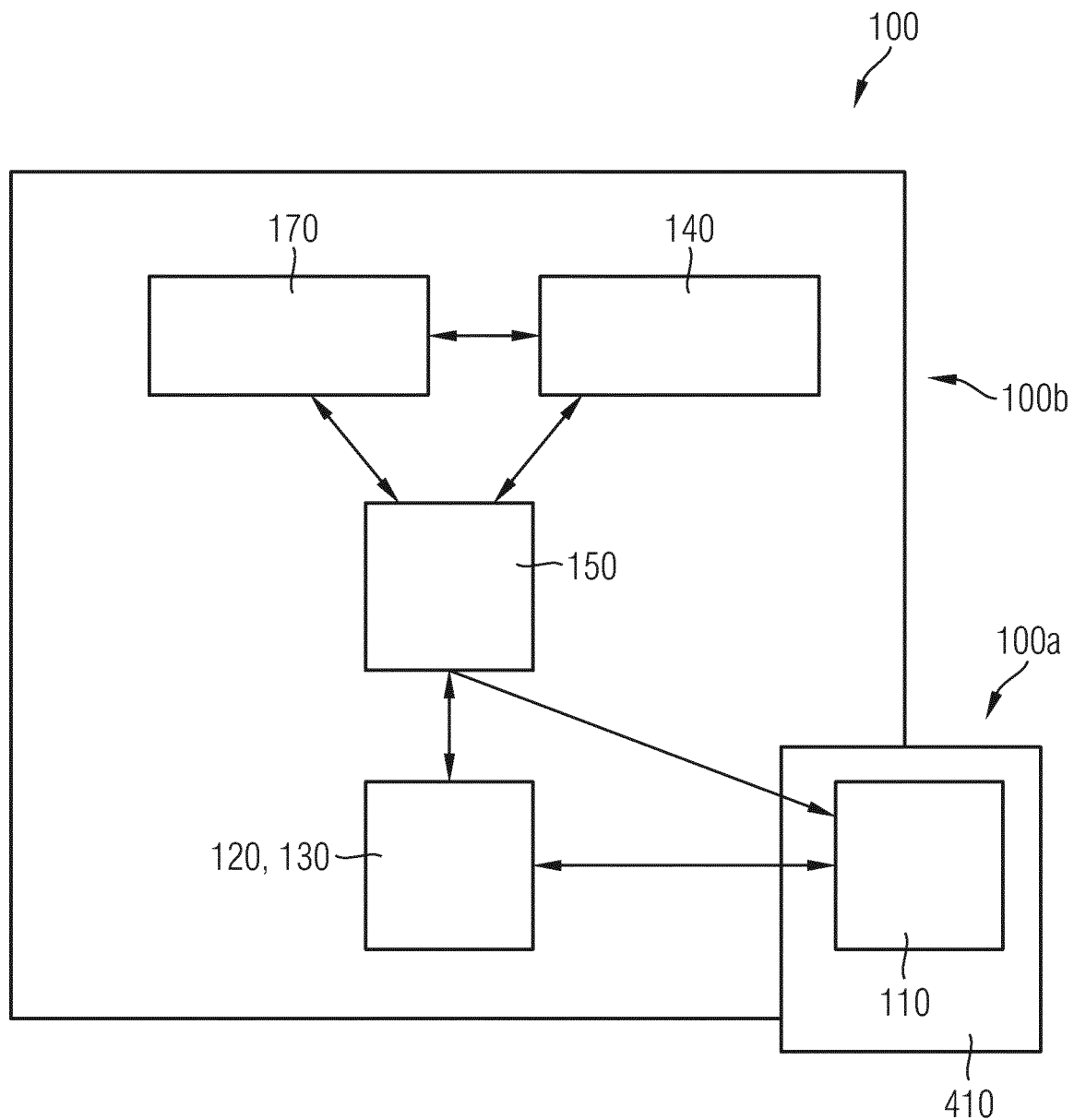
Figure 3D:
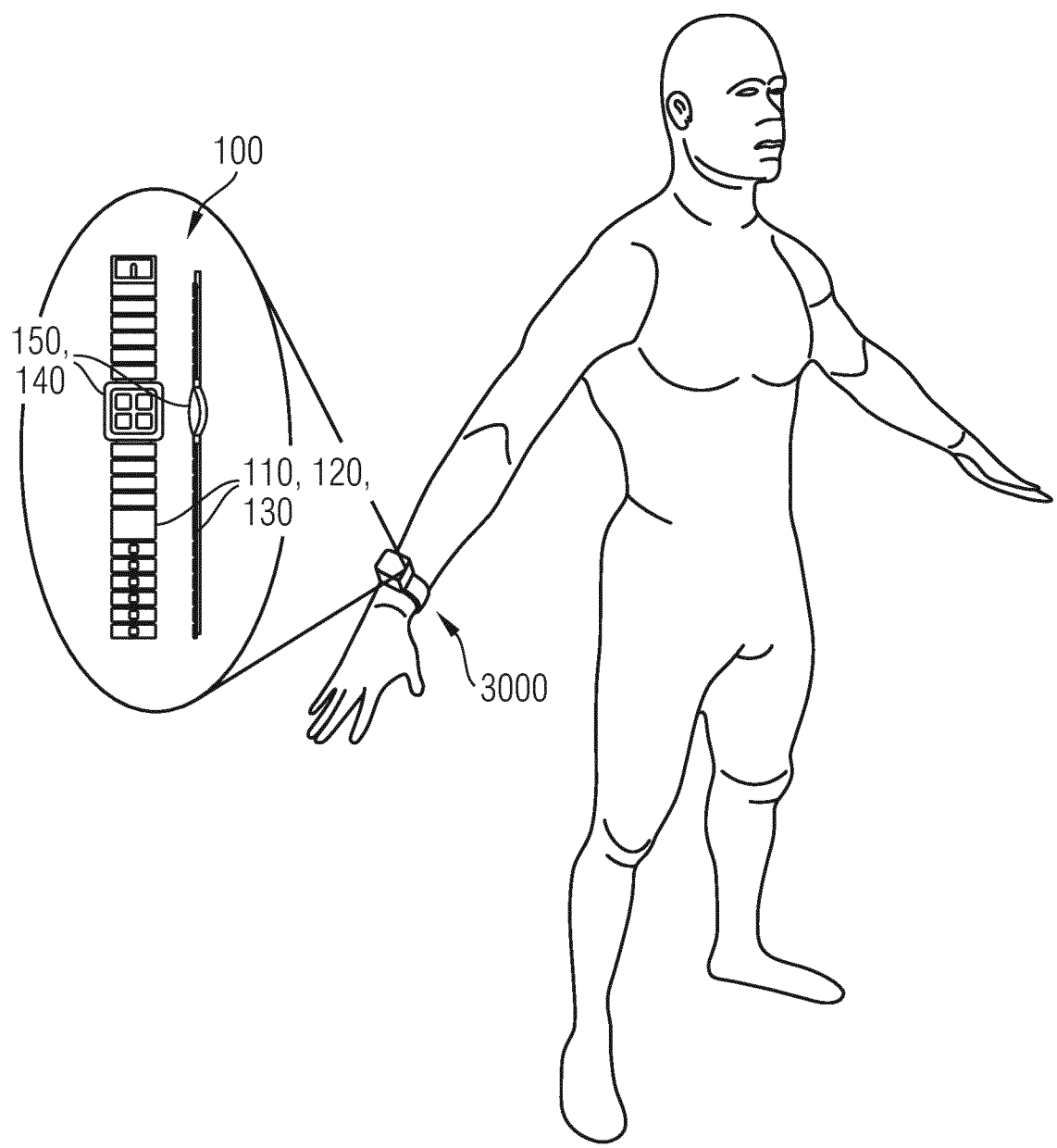
FIG. 3D is a schematic perspective view of a wrist watch including an electromagnetic wave sensor according to one or more embodiments.

FIG. 2C is a schematic block diagram of an electromagnetic wave sensor 100 according to an embodiment. As can be seen from FIG. 2C, the electromagnetic wave sensor 100 may be separated into two parts, a disposable part 100a and a non-disposable part 100b. In the disposable part 100a of the electromagnetic wave sensor 100, the waveguide unit 110, the electromagnetic wave transmitter unit 120 and the electromagnetic wave receiver unit 130 are integrated. In the non-disposable part of the electromagnetic wave sensor 100, the processor unit 150, the communication unit 140 and the energy storage unit 170 are integrated. As can be further seen from the embodiment of FIG. 2D, only the waveguide unit 110 may be integrated in the disposable part 100a, wherein the electromagnetic wave transmitter unit 120, the electromagnetic wave receiver unit 130, the processor unit 150, the communication unit 140 and the energy storage unit 170 may be integrated in the non-disposable part 100b of the electromagnetic wave sensor 100.

A product implementation of an electromagnetic wave sensor 100 having a disposable part 100a and a non-disposable part 100b is shown in FIGS. 3B and 3C. Herein, the disposable part 100a of the electromagnetic wave sensor 100 is the skin patch 400 comprising the skin patch body 410 and the waveguide unit 110 integrated in the skin patch body 410. The remaining electronic components are provided as a non-disposable part 100b, which may be integrated in a monolithic circuit 500.

As can be seen from FIG. 3C, the electromagnetic wave sensor 100 may be also integrated in a system 300 for determining a hydration status of a body tissue 10 in vivo, wherein the data from the electromagnetic wave sensor 100 related to the electromagnetic wave signal modified by the body tissue 10 in dependence of the hydration status of the body tissue 10 are transmitted to the external device 200. Herein, the external device 200 may comprise the processor unit 150 adapted to determine the hydration status of the body tissue 10 from the data transmitted by the electromagnetic wave sensor 100. The external device 200 is illustrated as a cellular phone. However, the external device 200 may be one of a group comprising a mobile device fixed to an armband or to a belt, a cellular phone, a smart phone, a personal computer, a tablet personal computer, a wrist watch, a smart watch, glasses or a bedside device.

As can be seen from FIG. 3C, the communication unit 140, the electromagnetic wave transmitter unit 120 and the electromagnetic wave receiver unit 130 of the electromagnetic wave sensor 100 may be integrated in a monolithic circuit 500. The electromagnetic wave transmitter unit 120 and the electromagnetic wave receiver unit 130 may be connected to the waveguide unit 110, wherein the waveguide unit 110 is integrated in the skin patch 400. According to another embodiment, the waveguide unit 110 may also be integrated in the monolithic circuit 500, which is the embedded in the skin patch body 410. Since the components of the hydration sensor can be monolithically integrated, the device can take the form of a textile band or a tattoo that can be adhered to the skin.

Thus, the electromagnetic wave sensor 100 can either be realized with a direct user interface or incorporates a communication unit 140. Therefore, the information about the dehydration or hydration status measured by the electromagnetic wave sensor 100 can be transferred via wireless communications to an external device 200 in order to provide the interface with the user. The fact, that the graphical user interface 190 is concentrated in one device, allows also the possibility to manage not only an electromagnetic wave sensor 100 but also an array of sensors such as the skin patches 400 shown in FIG. 3C adhered to the users body. As the electromagnetic wave sensor 100 is monolithically integrated in a monolithic circuit 500, this can be in form of a disposable material. The electromagnetic wave sensor 100 can be also integrated in a wearable device like a wrist watch 3000 or a wristband. This realization includes the graphical user interface 190 and requires no communication unit 140.

The size of the electromagnetic wave sensor 100 is substantially limited by the wavelength of the emitted electromagnetic wave signal. Taking an electromagnetic wave frequency for probing the body tissue 10 of 3 GHz to 30 GHz (Super High Frequency region), the freespace wavelength is in the order of 10 cm to 1 cm. In case of choosing electromagnetic waves in a frequency range of 30 GHz to 300 GHz (Extremely Frequency region) the freespace wavelength is in a range of 1 cm to 1 mm. The electromagnetic wave frequency may even be higher in a range of 300 GHz to 3 THz, leading to a freespace wavelength in a sub-millimeter-range. Thus, the higher the probing electromagnetic wave signal frequency, the smaller the electromagnetic wave sensor 100 can be designed.

Figure 4A:
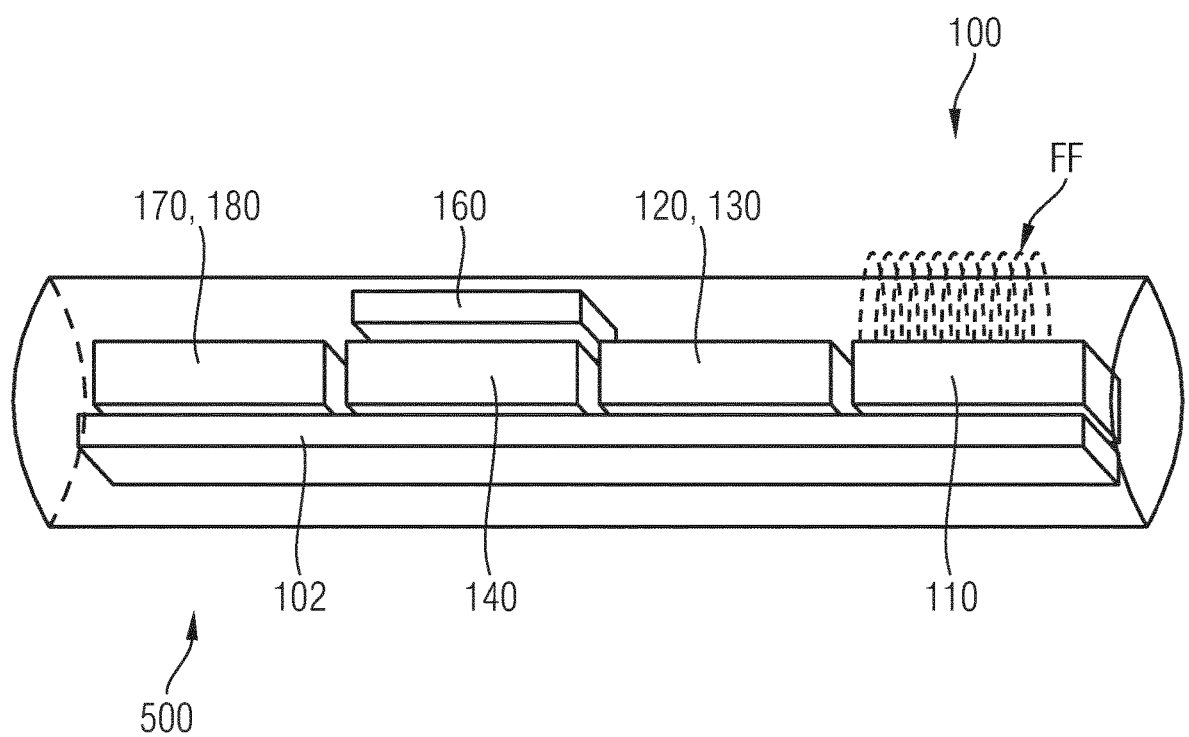
FIG. 4A is a schematic block diagram of an electromagnetic wave sensor integrated in a monolithic circuit according to one or more embodiments.
Figure 4B:
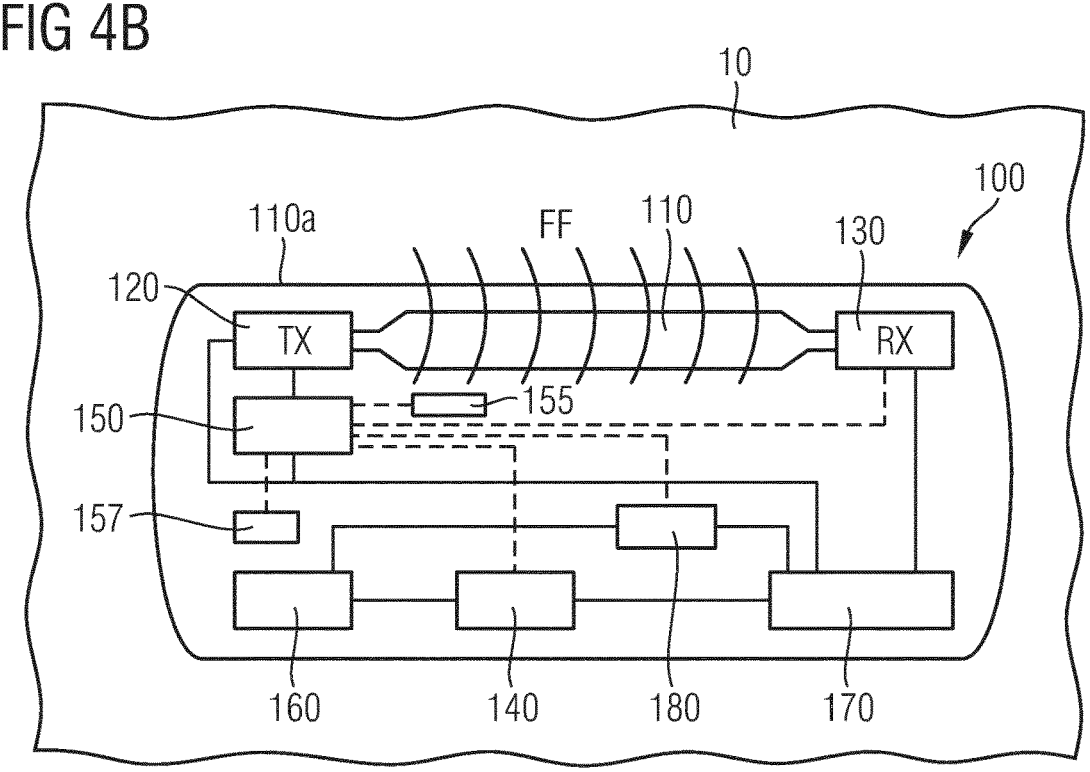
FIG. 4B is a schematic block diagram of an electromagnetic wave sensor according to one or more embodiments.

FIGS. 4A and 4B are schematic block diagrams of an electromagnetic wave sensor 100 for determining a hydration status of a body tissue in vivo according to an embodiment.

FIG. 4A illustrates an electromagnetic wave sensor 100 integrated in a monolithic circuit 500. Herein, the waveguide unit 110, the electromagnetic wave transmitter unit 120 the electromagnetic wave receiver unit 130, the communication unit 140, the energy storage unit 170, the energy harvesting unit 180, an antenna unit 160 may be integrated on a semiconductor substrate 102 as one integrated circuit.

According to another embodiment, the waveguide unit 110 as shown in FIG. 4A may be integrated in the skin patch 400, wherein the electromagnetic wave transmitter unit 120 and the electromagnetic wave receiver unit 130 may be adapted to be connected to the waveguide unit 110 via a plug and socket connection. In such an embodiment, the monolithic circuit 500 may be accommodated in a pocket of the skin patch 400, and after disposal of the skin patch body 410 and the integrated waveguide unit 110, the monolithic circuit 500 may be reused after sterilizing the same in an autoclave unit or by sterilizing the same in an alcohol bath. In the sterilizing process, the energy storage unit 170 may be supplied with energy via the energy harvesting unit 180 harvesting electromagnetic wave energy from an external energy source.

As can be seen from FIG. 4B, the electromagnetic wave sensor 100 comprises the electromagnetic wave transmitter unit 120 (indicated as TX) configured to emit an electromagnetic wave signal penetrating the body tissue 10, the electromagnetic wave receiver unit 130 (indicated as RX) configured to receive the electromagnetic wave signal modified by the body tissue 10, and the communication unit 140 configured to transmit radio frequency signals related to the electromagnetic wave signal modified by the body tissue 10.

The electromagnetic wave sensor 100 may further comprise a processor unit 150, which is connected via a data line (indicated by the dotted line) with the electromagnetic wave transmitter unit 120 and the electromagnetic wave receiver unit 130. The processor unit 150 is configured to process parameters of the emitted electromagnetic wave signal, which are received from the electromagnetic wave transmitter unit 120 via the data line, and to process parameters of the electromagnetic wave signal modified by the body tissue 10, which are received from the electromagnetic wave receiver unit 130 via the data line. The processor unit 150 may be further connected via a data line to a memory unit 155, which is configured to store measurement raw data or processed data from the processor unit 150. The processor unit 150 is further connected via a data line to the communication unit 140, to provide the communication unit 140 with processed data to be transmitted to an external device 200 via an antenna unit 160. The units 120 to 150 are powered via power lines (indicated by a continuous line) from an energy storage unit 170. The energy storage unit 170 may be charged by an energy harvesting unit 180 which may be connected to the antenna unit 160, thus using the antenna unit 160 in common with the communication unit 140. Furthermore, according to an embodiment, the electromagnetic wave sensor 100 may comprise a temperature sensor 157 for measuring the temperature of the body tissue 10. The temperature data is transmitted to the processor unit 150, to consider a temperature variation of the body tissue 10 in the analysis of the hydration status. Although a possible temperature change of a human is low in view of the absolute temperature (310 K±5 K), it has been found that the temperature of the body tissue 10 may have a non-negligible influence on the transmission or reflection spectra of the electromagnetic waves in the microwave range, millimetre wave range or sub-millimetre wave range.

Figure 5A:
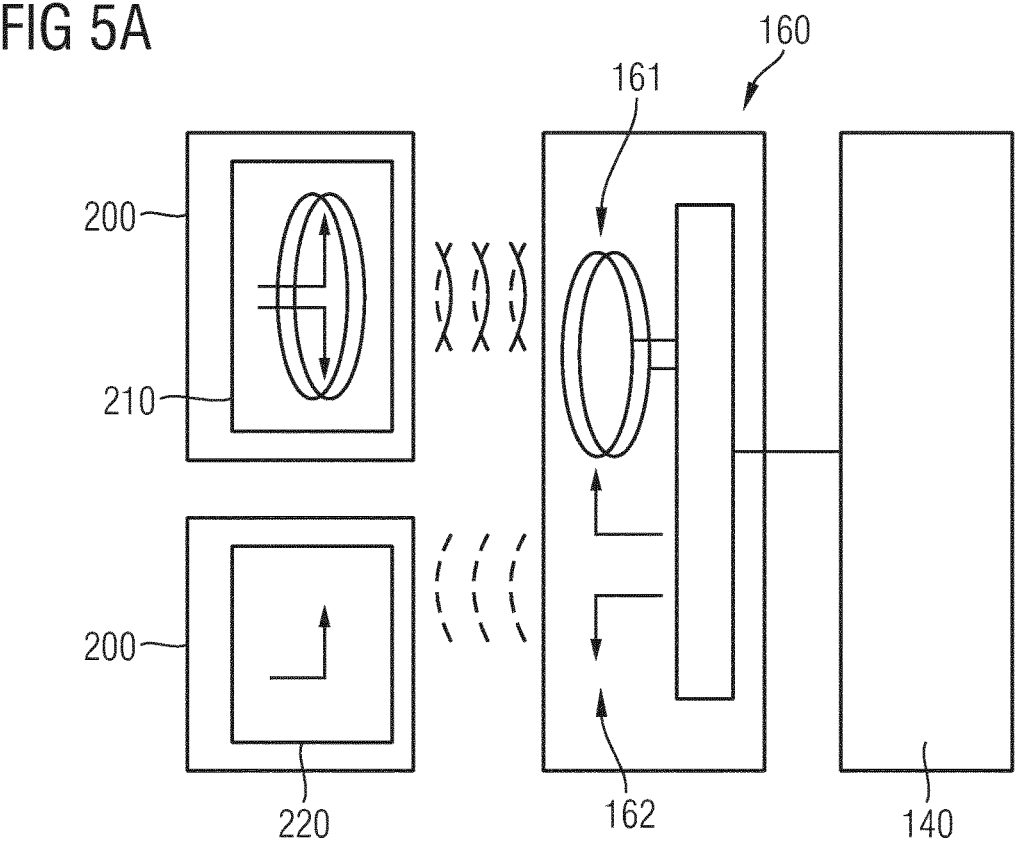
FIG. 5A is a schematic block diagram of an antenna unit of the electromagnetic wave sensor in communication with an external device according to one or more embodiments.

In the following, the above units shall be described in more detail. FIG. 5A is a schematic block diagram of the antenna unit 160 and a communication unit 140 communicating with an external device 200. The wireless communication of the communication unit 140 with the external device 200 may include a plurality of different wireless communication protocols and various communication frequency bands. The communication unit 140 may also receive update programs from the external device to adapt a communication procedure with the external device. The update programs may also be provided for updating an operating system of the processor unit 150. In the embodiment shown in FIG. 5A, the antenna unit 160 may comprise at least one of a radio frequency identification (RFID)/near field communication (NFC) antenna 161 communicating with the respective antenna 210 within the external device 200 and an RFID/ultra-high frequency (UHF) antenna 162 communicating with the respective antenna 220 within the external device 200.

RFID devices operate at different radio frequency ranges, e.g. low frequency (LF) at about 28 to 135 kHz, high frequency (HF) at about 13.56 MHz, and ultra-high frequency (UHF) at 860 to 960 MHz. Each frequency range has unique characteristic in terms of RFID performance.

NFC is a short range technology that enables two devices to communicate when they are brought into actual touching distance. NFC enables sharing power and data using magnetic field induction at 13.56 MHz (HF) band, at short range, supporting varying data rates from 106 kbps, 212 kbps to 424 kbps. A key feature of NFC is that is allows two devices to interconnect. In reader/writer mode, an NFC tag is a passive device that stores data that can be read by an NFC enable device. In peer-to-peer mode, two NFC devices can exchange data. Bluetooth or WiFi link set up parameters can be shared using NFC and data such as virtual business cards or digital photos can be exchanged. In card emulation mode, the NFC device itself acts as an NFC tag, appearing to an external interrogator as a traditional contact less smart card. These NFC standards are acknowledged by major standardisation bodies and based on ISO/IEC 18092.

Passive UHF systems use propagation coupling, where an interrogator antenna emits electromagnetic energy radio frequency waves and the RFID tag receives the energy from the interrogator antenna, and the integrated circuit uses the energy to change the load on the antenna and reflect back an altered signal that is then demodulated. For the LF and HF RFID systems using interactive coupling, the range of the interrogator field is small (0.2 to 80 cm) and can be relatively easily controlled. UHF systems that use propagation coupling are harder to control, because energy is sent over long distances. The radio waves can reflect on hard surfaces and reach tags that are not in the normal range. LF and HF systems perform better than UHF systems around metal and water. The radio waves do reflect off metal and cause false reads, and they are better able to penetrate water. UHF radio waves are attenuated by water.

In addition, communication may be performed via any one of an Industrial, Scientific and Medical (ISM) Band, which operates in a frequency range between 6.765 MHz to 246 GHz and has bandwidths of up to 2 GHz.

Figure 5B:
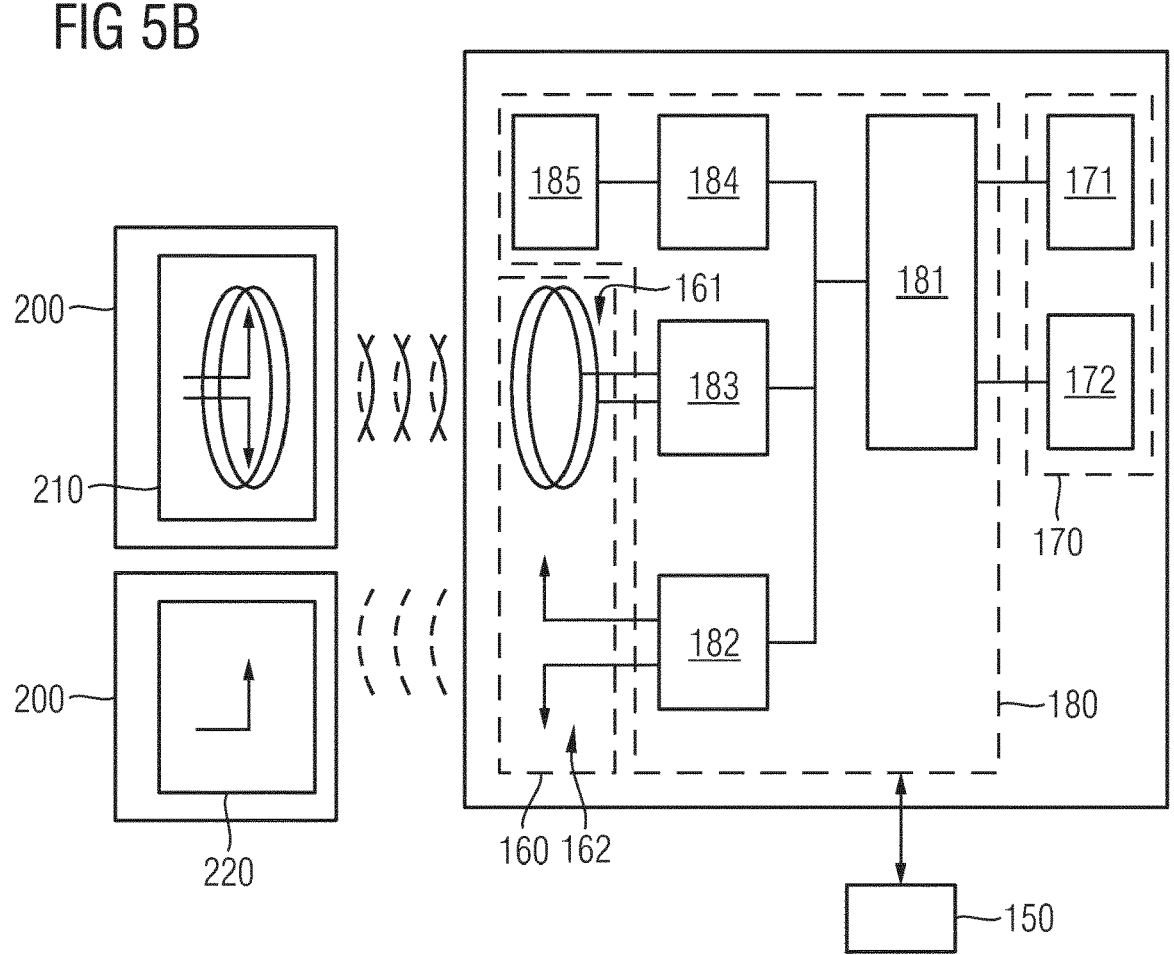
FIG. 5B is a schematic block diagram of an antenna unit, an energy storage unit, an energy harvesting unit, and a processor unit of the electromagnetic wave sensor being in communication with an external device according to one or more embodiments.

FIG. 5B is a schematic block diagram showing the energy harvesting unit 180 being connected to the antenna unit 160, to harvest energy from an external power source, e.g. the external device 200, for charging an energy storage unit 170. The energy harvesting unit 180 may be controlled by the processor unit 150. The energy harvesting unit 180 comprises a power management unit 181, which is connected to a HF power converter 183 for converting power from the RFID/NFC antenna 161 and is further connected to an UHF power converter 182, which is connected to the RFID/UHF antenna 162 of the antenna unit 160.

Energy may be harvested through a dedicated radio frequency source, and energy may be harvested from ambient radio frequency. The HF power converter 183 connected to the RFID/NFC antenna 161 is able to harvest energy from different external devices 200 such as smartphones or RFID devices to power data transmission. The UHF power converter 182 connected to the RFID/UHF antenna 162 is able to harvest ambient radio frequency energy from existing external energy sources like TV signal, WiFi/WiMAX, GSM and others. Furthermore, the energy harvesting unit 180 may comprise a DC to DC converter 184 connected to a thermal or piezoelectric harvester 185. Herein, kinetic energy may be harvested to obtain energy from human motion.

The energy storage unit 170 may comprise a chargeable storage device 171. Herein, a silicon-based rechargeable lithium battery may be used. As silicon has highest lithium ion storage capacity/volume, even a very tiny-sized battery (A<1 mm$^2$) may provide storage capacity in the order of up to 250 to 500 µAh, which is sufficient for various applications. The energy storage unit 170 may further comprise a capacitor 172. Herein, printed energy storage devices or printed supercapacitors may be used.

As shown in FIG. 4B, the electromagnetic wave sensor 100 further comprises the waveguide unit 110 coupled to the electromagnetic wave transmitter unit 120 and the electromagnetic wave receiver unit 130, wherein the waveguide unit 110 is arranged such that a fringe field of the electromagnetic wave signal of the waveguide unit 110 penetrates the body tissue 10. As shown in the embodiment of FIG. 4B, the electromagnetic wave transmitter unit 120 and the electromagnetic wave receiver unit 130 may be arranged at opposite ends of the waveguide unit 110. Thus, a forward transmission factor may be determined. However, it is also possible to arrange the electromagnetic wave transceiver unit 120 and the electromagnetic wave receiver unit 130 at a same end of the waveguide unit 110, as shown, for example in FIG. 7B or 7C. According to the embodiment of FIG. 7B, the electromagnetic wave transmitter unit 120 may be embodied as an electromagnetic wave transceiver unit, wherein the electromagnetic wave receiver unit 130 is not arranged at the opposite end of the waveguide unit 110. However, as can be seen from FIG. 7C, the electromagnetic wave receiver unit 130 may be arranged at the opposite end of the waveguide unit 110 in addition to providing an electromagnetic wave transceiver unit at the end opposite to the electromagnetic wave receiver unit 130. In the measurement arrangement of FIGS. 7B and 7C, an input reflection factor may be determined. The electromagnetic wave transmitter unit 120 (as transmitter or transceiver) and the electromagnetic wave receiver unit 130 may also be embodied as one unit, for example integrated in a monolithic circuit 500.

The length of the waveguide unit 110 may be quarter or half of a maximum guided wavelength of the electromagnetic wave signal emitted by the electromagnetic wave transceiver unit 120 to ensure an optimized emission characteristics of the waveguide unit 110. The term guided wavelength will be discussed below.

Figure 5C:
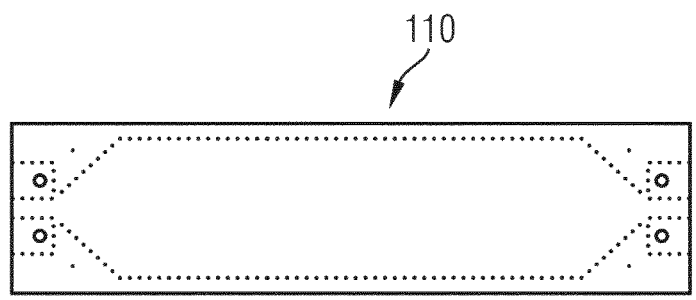
FIG. 5C is a schematic plan view of a waveguide unit of the electromagnetic wave sensor according to one or more embodiments.
Figure 5D:
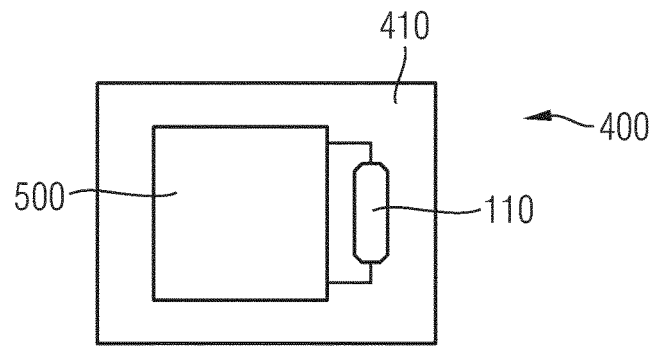
FIG. 5D is a schematic plan view of an electromagnetic wave sensor integrated in a monolithic circuit and being connected to a waveguide unit integrated in a skin patch according to one or more embodiments.

FIG. 5C is a plan view of a waveguide unit 110, wherein the waveguide unit 110 is embodied as a microstrip line. As shown in FIG. 5D, the waveguide unit 110 may also be arranged on a chip surface in case the electromagnetic wave sensor 100 is integrated in the monolithic circuit 500, e.g. of a silicon chip.

Figure 5E:
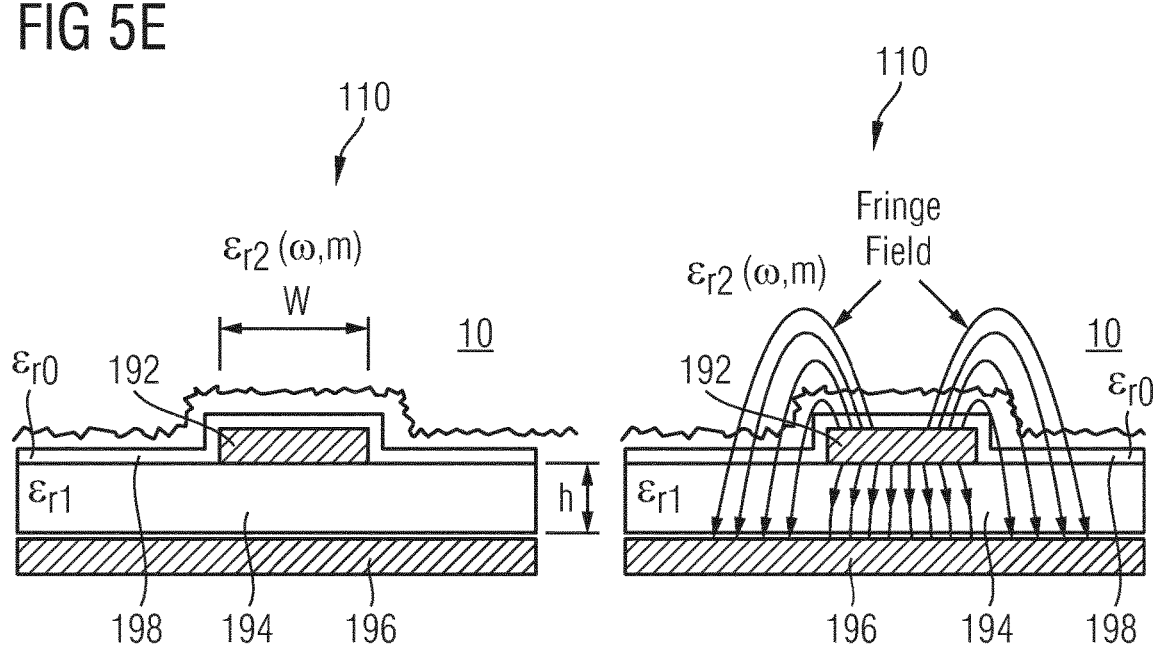
FIGS. 5E and 5F are schematic cross-sectional views of portions of a waveguide unit of the electromagnetic wave sensor according to different embodiments.

The principle of the emission of a fringe field of the waveguide unit 110 is illustrated in FIG. 5E. In the waveguide unit 110, the electric and magnetic fields are only partially contained within the waveguide unit 110, because the conductor is not wholly shielded. Although the term "waveguide" is used, it should be emphasized that this term is not to be understood as a perfect waveguide, in which the electromagnetic field is fully shielded but as a dielectrically loaded waveguide or transmission line, in which a fringe field is extended into the interstitial fluid to be probed by the same. The waveguide unit shown in FIG. 5E comprises a signal guiding line 192, e.g. of a metal such as copper, provided on a dielectric substrate 194 having a permittivity $\varepsilon_{r1}$ and made of a ceramic or plastic material, for example. On a surface of the dielectric substrate 194 opposite to the signal guiding line 192, a conductive layer 196 is provided, acting as ground for the signal guiding line 192. A passivation layer 198 having a permittivity $\varepsilon_{r0}$ may further be provided, covering the dielectric substrate 194 and the signal guiding line 192.

If the waveguide unit 110 is brought in contact with a body containing the body tissue 10, the fringing field outside the substrate may interact with the body tissue 10. The fringing field can penetrate the body tissue 10 and on this way can interact with the body tissue 10 having a permittivity $\varepsilon_{r2}$. The interaction between the body tissue 10 and the waveguide unit 110 can be modelled through the effective permittivity on the waveguide unit 110 as shown in FIGS. 5C and 5D, wherein the permittivity of the thin passivation layer 198 has been be neglected.

$$\varepsilon_{\mathit{eff}} = \varepsilon_{r1} q_1 + \varepsilon_{r2} \frac{(1-q_1)^2}{\varepsilon_{r2}(1-q_1-q_2)+q_2} \tag{1}$$

In formula (1), $q_1$ and $q_2$ are the ratios of the electromagnetic field energy in the dielectric substrate 194 having the permittivity $\varepsilon_{r1}$ and the body tissue 10 having the permittivity $\varepsilon_{r2}$, respectively. $q_1$ and $q_2$ are values in a range between 0 and 1. The wavelength of the electromagnetic wave guided in the waveguide unit 110 is indicated as guided wavelength $\lambda_g$, wherein the corresponding wavelength in vacuum is indicated as freespace wavelength $\lambda_0$. The relation between $\lambda_0$ and $\lambda_g$ is as follows:

$$\lambda_g = \lambda_0 / \sqrt{\varepsilon_{\mathit{eff}}} \tag{2}$$

As can be seen from formula (2), the guided wavelength may be significantly smaller than the freespace wavelength. Taking, for example, an $\varepsilon_{\mathit{eff}}$ of about 80, the guided wavelength is almost one order of magnitude smaller than the freespace wavelength. Since the body tissue 10 is a fluid composed of significant amount of water, it can be modelled as an aqueous solution for a first approximation. The permittivity $\varepsilon_{r2}$ can be described as a Debye model that is a function of frequency $\omega$ and glucose concentration $\chi$ as follows:

$$\varepsilon_{r2}(\omega, \chi) = \varepsilon_\infty(\chi) + \frac{\varepsilon_{stat}(\chi) - \varepsilon_\infty(\chi)}{1 + j\omega\tau(\chi)} \quad (3)$$

In formula (3), $\varepsilon_\infty$, $\varepsilon_{state}$ and $\tau$ are static and infinity permittivity and the relaxation time, respectively. In consideration of the relation between the propagation characteristics and the effective permittivity of the waveguide unit 110, the attenuation constant and the wave number of the waveguide unit 110 are also a function of the hydration status within the body tissue 10.

The propagation constant of the electromagnetic wave in a dielectric medium is a function of the permittivity:

$$\varepsilon_r = \varepsilon' - j\varepsilon'' \quad (4)$$

and can be expressed as:

$$\gamma = \alpha + j\beta \quad (5)$$

The attenuation constant $\alpha$ and the wave number $\beta$ can be expressed as a function of the permittivity of the material:

$$\alpha = -\frac{\omega\sqrt{\varepsilon_r}}{c_0}\sqrt{\frac{1}{2}\left(\sqrt{1 + \left(\frac{\varepsilon_r''}{\varepsilon_r'}\right)^2} - 1\right)} \quad (6)$$

$$\beta = \frac{\omega\sqrt{\varepsilon_r}}{c_0}\sqrt{\frac{1}{2}\left(1 + \sqrt{1 + \left(\frac{\varepsilon_r''}{\varepsilon_r'}\right)^2}\right)} \quad (7)$$

It is known that the permittivity of a material is a function of the frequency $\omega$ and the moisture content of the material m:

$$\in_2(\omega,m) = \varepsilon'(\omega,m) - j\varepsilon''(\omega,m) \quad (8)$$

Therefore, the attenuation constant and the wave number can be expressed also as a function of the moisture content as follows:

$$\alpha = -\frac{\omega\sqrt{\varepsilon_r'(\omega, m)}}{c_0}\sqrt{\frac{1}{2}\left(\sqrt{1 + \left(\frac{\varepsilon_r''(\omega, m)}{\varepsilon_r'(\omega, m)}\right)^2} - 1\right)} \quad (9)$$

$$\beta = \frac{\omega\sqrt{\varepsilon_r'(\omega, m)}}{c_0}\sqrt{\frac{1}{2}\left(1 + \sqrt{1 + \left(\frac{\varepsilon_r''(\omega, m)}{\varepsilon_r'(\omega, m)}\right)^2}\right)} \quad (10)$$

A microwave signal may be transmitted along an open waveguide in a similar manner to transmission on a co-axial transmission line but, in open waveguides, the electric and magnetic fields are only partially contained within the waveguide, because the conductor is not wholly shielded. The fringing field outside the substrate may interact with the tissue brought into contact with the open waveguide. The fringing field penetrates through the skin and on this way interacts with the blood of superficial blood vessels, this interaction results in a relation between the water content of the blood and the propagation characteristics of the open wave guide. In other words, the transmission and the reflection properties of the open wave guide become a function of the blood water level.

Figure 5F:
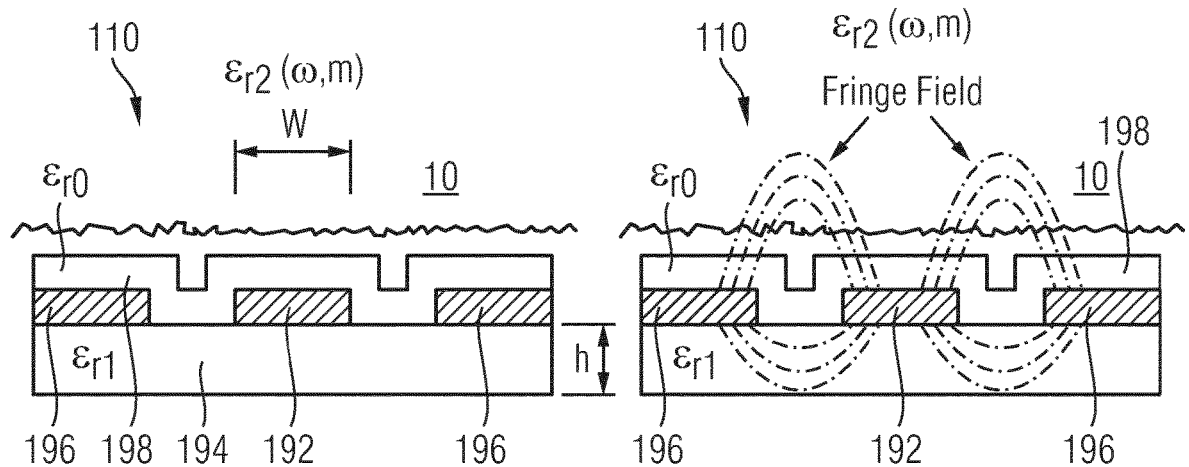

FIG. 5F shows another embodiment of a waveguide unit 110. According to the embodiment of FIG. 5E, the waveguide unit 110 is a microstrip line. According to the embodiment of FIG. 5F, the waveguide unit 110 is a coplanar waveguide. The elements of the waveguide unit 110 of FIG. 5F and of the waveguide unit 110 of FIG. 5F are basically the same. However, in the waveguide unit 110 being a coplanar waveguide, the signal guiding line 192 and the conductive layer 196, acting as ground for the signal guiding line 192, are provided on the same surface of the dielectric substrate 194.

Figure 5G:
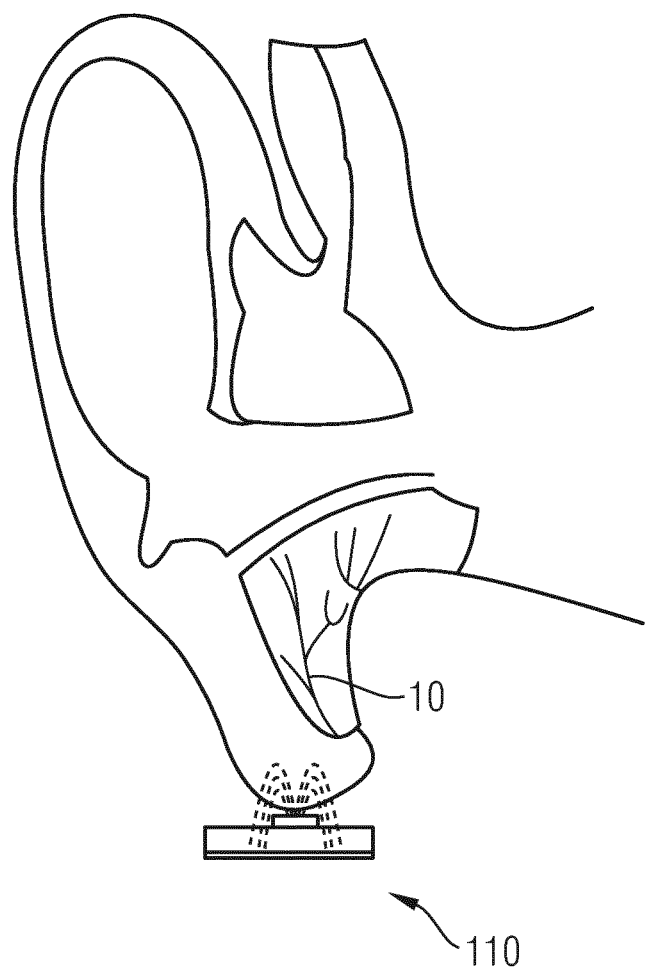
FIG. 5G is a schematic view of a waveguide unit being arranged next to an ear portion of a human body such that a fringe field of the electromagnetic wave signal guided by the waveguide unit penetrates the body tissue of the ear portion of the human according to one or more embodiments.

As can be seen from FIG. 5G, an example of an arrangement of a waveguide unit 110 is shown. Herein, a waveguide unit of FIG. 5E is placed at an earlobe of a user. The best places to measure the dehydration level with the waveguide unit 110 are superficial arteries (such as the radial artery, the carotid artery, the femoral artery or the temporal artery) or places with rich blood irrigation like the earlobe.

In comparison with resonant sensors like antennas or ring resonators, sensors based on waveguides are ultra-wideband structures, allowing to cover a big portion of the spectrum only with one structure. By covering an ultra-wideband spectrum, different effects that are a function of the frequency will be taken in account.

The hydration of the different tissue layers between the waveguide unit 110 and a blood vessel (skin, fat, muscle and body fluid) can be compensated taking advantage of the dielectric properties of each layer. Lower frequency are used to characterize the deepest tissue (fat, muscle and body fluid) and higher frequencies are used to characterize the skin properties and the skin humidity.

Figure 5H:
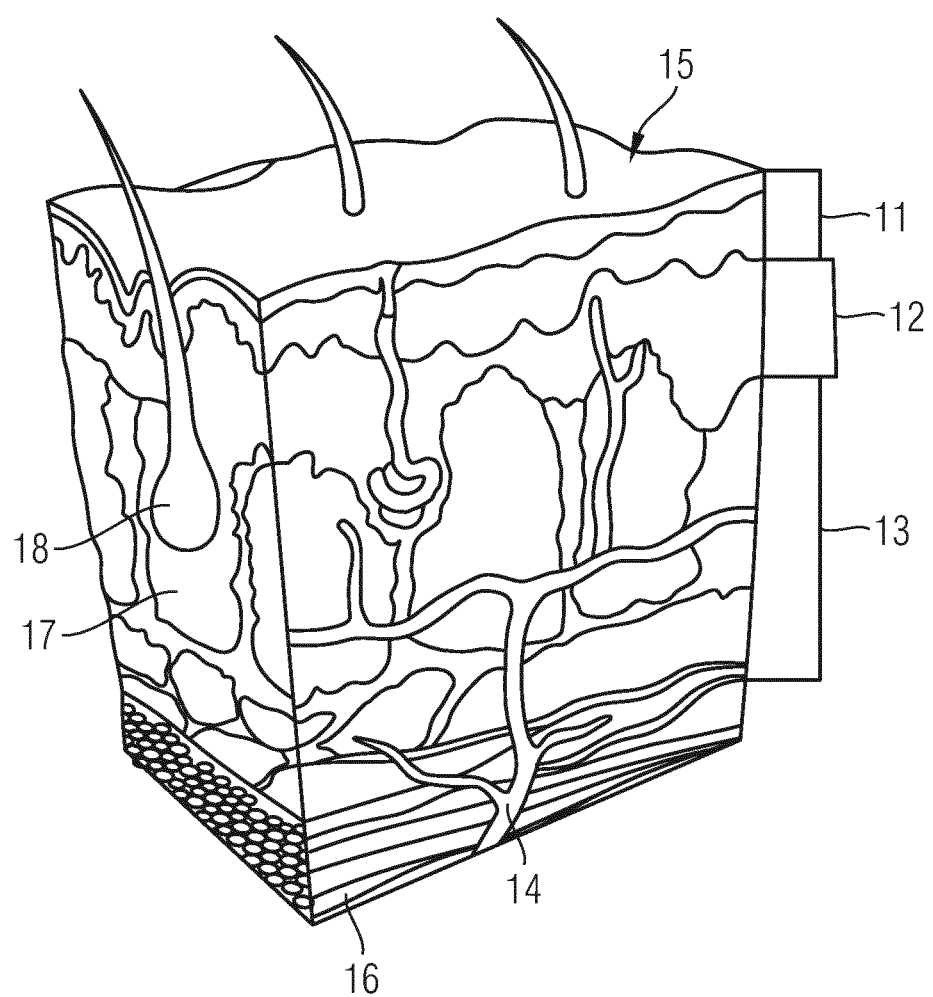
FIG. 5I is a schematic cross-sectional view of a body tissue according to one or more embodiments.

In FIG. 5H an example of tissue layers between the waveguide unit 110 and the blood vessel are shown. Herein, the skin 15 can be separated in an epidermis layer 11, a dermis layer 12 and a hypodermis layer 13. Under hair follicles 18 embedded in a fat layer 17, the muscle layer 16 and the blood vessel 14 are located in the body tissue 10.

One important part in the determination of the hydration is the measurement of the concentration of electrolytes in the blood. The concentration of electrolytes is measured by using the effect caused by the unique relaxation on the propagation constant of the waveguide unit 110. The unique relaxation has an influence especially for frequencies below 1 GHz. On the other side, the system composed by the cell membrane and the cell content, can be modelled as a highpass filter. By existing the body tissue 10 with a low frequency microsignal, the extracellular water content will be determined. To determine the intracellular water content, higher frequencies are used to measure the total water content (intracellular and extracellular).

Figure 5I:
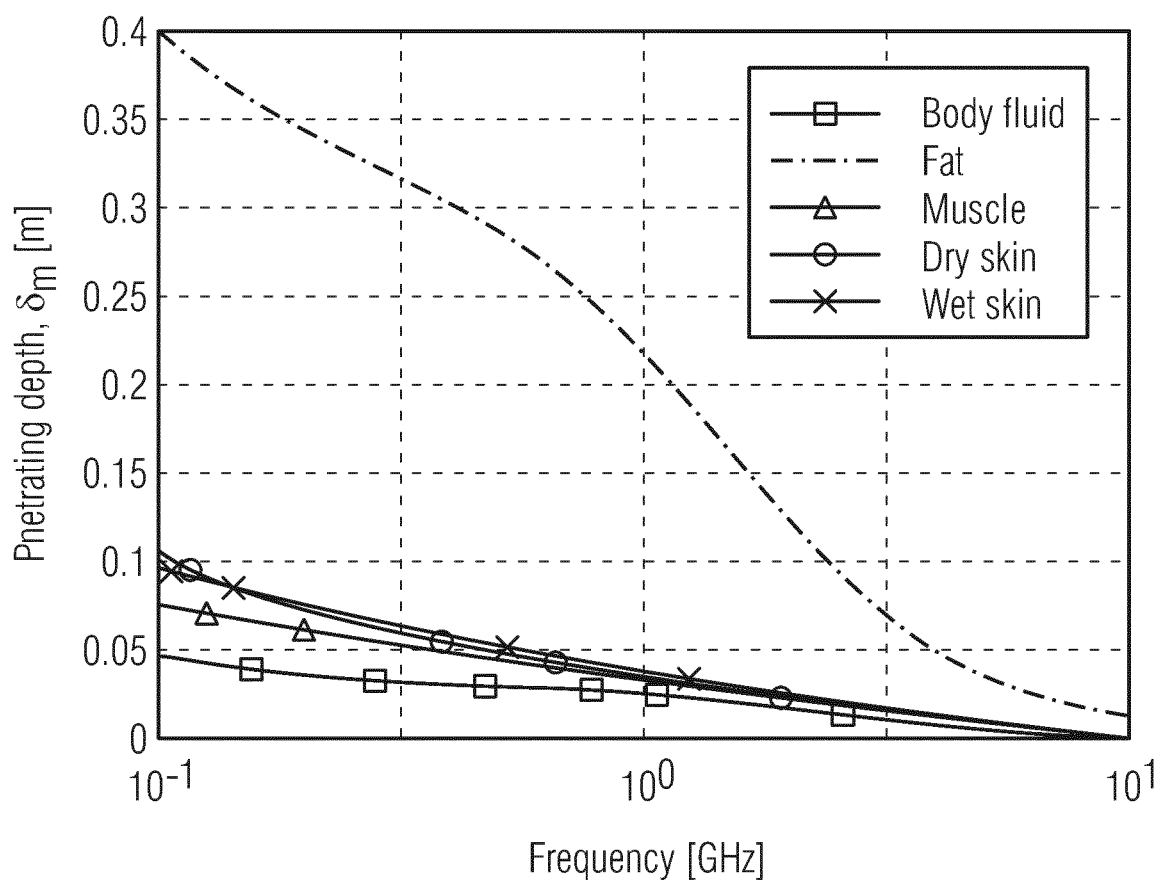

In FIG. 5I, a penetrating depth of a microwave signal for different tissues as a function of the frequency is shown. As can be seen from FIG. 5I, by using different frequencies ranges of the microwave signal, different tissue parts of the body tissue 10 at different depths can be investigated. To determine the hydration status of the body tissue 10, the processor unit 150 may be adapted to determine the hydration status on the basis of a frequency analysis of a transfer function of the propagation constant of the waveguide unit 110 between the electromagnetic wave transmitter unit 120 and the electromagnetic wave receiver unit 130. Herein, the processor unit 150 may be adapted to determine the hydration status on the basis of a frequency shift of a peak in the transfer function depending on the hydration status. As will be discussed in the following, the electromagnetic wave transmitter unit 120 may be adapted to sweep the frequency of the electromagnetic wave signal in a frequency range having a bandwidth of at least 5 GHz, or at least 10 GHz, or at least 50 GHz, or at least 100 GHz, or at least 500 GHz. According to another embodiment, the electromagnetic wave transmitter unit 120 may be adapted to emit an electromagnetic wave signal having frequency components within a frequency bandwidth of at least 5 GHz, or at least 10 GHz, or at least 50 GHz, or at least 100 GHz, or at least 500 GHz.

Thus, the frequency shift in dependence on the hydration status may be used to determine the hydration status of the body tissue 10. Furthermore, the complete spectrum may be analysed to assign to each hydration status of the body tissue 10 a respective spectrum, e.g. by a learning algorithm or a reference database. Herein, raw data of the measured spectra of the body tissue 10 at different values of the hydration status may be transmitted from the communication unit 140 to the external device 200, wherein the hydration status is measured invasively, e.g. by blood withdrawal. The respective spectra are then correlated with the invasively measured hydration status in a learning phase of the implanted electromagnetic wave sensor 100. The shift of different maxima of the electromagnetic wave transmission spectrum may occur in both directions, thus a characteristic signature may be determined, which reduces the influence of parameters being different from the hydration status of interest. The measured spectra may be different for different implantation environments, however the differential behaviour of the spectra in dependence of the hydration status ensures a definite detection of the hydration status.

The frequency range of the electromagnetic wave sensor 100 may be the microwave range between 300 MHz and 30 GHz, and/or the millimeter wave range between 30 GHz to 300 GHz, and/or the sub-millimeter range between 300 GHz to 3 THz. For providing the possibility of a broadband analysis of the transmission and/or reflection spectra of the emitted electromagnetic waves, the electromagnetic wave transmitter unit 120, the waveguide unit 110 and the electromagnetic wave receiver unit 130 may be adapted for broadband emission, broadband guidance and broadband reception. Spectra of interest are parts of the electromagnetic spectrum, in which the body tissue transmission/reflection characteristic is strongly influenced by the presence of the hydration status. Interesting frequency ranges for hydration are frequencies around 8 GHz. Thus, according to an embodiment, the electromagnetic wave transmitter unit 120 may be configured to emit electromagnetic wave signals in a frequency range between 1 GHz and 25 GHz, or between 5 GHz and 15 GHz, or between 5 GHz and 10 GHz. Further interesting frequency ranges may be frequencies between 70 GHz and 80 GHz, frequencies between 150 GHz and 200 GHz, or frequencies up to 300 GHz. Thus, according to another embodiment, the electromagnetic wave transmitter unit 120 may be configured to emit electromagnetic wave signals in a frequency range between 300 MHz and 300 GHz, or between 1 GHz and 200 GHz, or between 1 GHz and 100 GHz, or between 1 GHz and 50 GHz. The electromagnetic wave transmitter unit 120 may be adapted to emit microwaves in a complete range of 300 MHz to 30 GHz. According to an embodiment, the bandwidth of the emitted electromagnetic wave signal of the electromagnetic wave transmitter unit 120 may be 500 GHz, or 200 GHz, or 100 GHz, or 50 GHz, or 30 GHz. According to an embodiment, the spectrum analysis of the interstitial fluid may be performed by sequentially switching harmonic frequencies to be emitted in a fringe field by the waveguide unit 110. To achieve a broadband analysis, at least two units comprising one electromagnetic wave transmitter unit 120, one waveguide unit 110 and one electromagnetic wave receiver unit 130 may be provided, which are specifically adapted for a certain frequency range, wherein all units cover a broad frequency range to be analysed.

Figure 6:
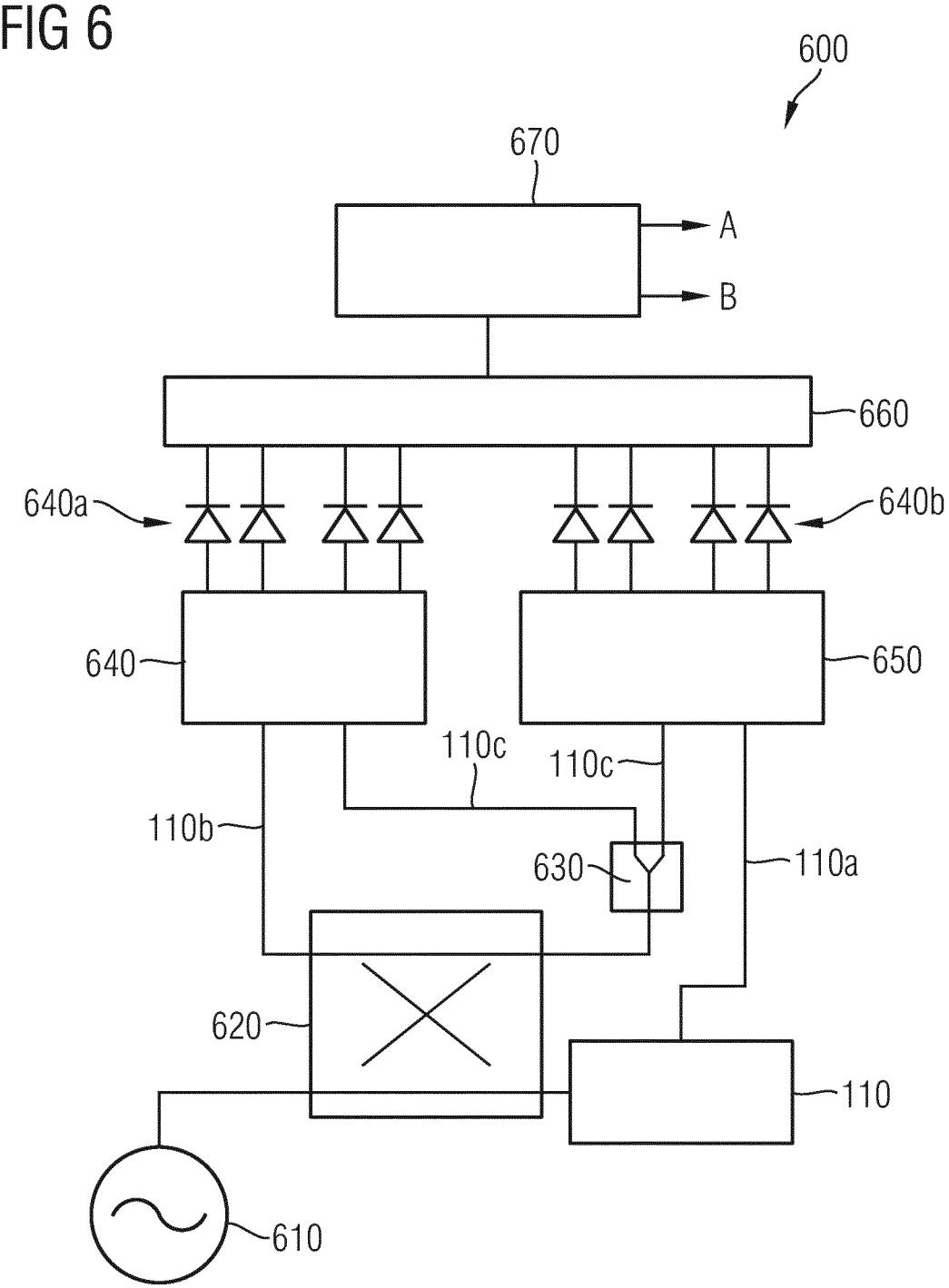
FIG. 6 is a schematic block diagram illustrating a six-port architecture for the characterization of a sensor propagation constant.

FIG. 6 is a schematic block diagram of a six-port architecture for determining a hydration status of a body tissue 10 in vivo according to an embodiment. As can be seen from FIG. 6, an radio frequency source 610 for providing frequencies between DC and 100 GHz is connected to the waveguide unit 110. The transmitted components of the electromagnetic wave signal on line 110a and the reflected components of the electromagnetic wave signal on line 110b are transferred together with a reference signal on line 110c to a passive six-port structure 640, 650. A bidirectional coupler 620 is provided between the radio frequency source 610 and the waveguide unit 110 as well as between the line 110b and a signal branching element 630. The signal from the passive six-port structure 640, 650 is down converted to baseband by diode detectors 640a, 650a, respectively. After analogue digital converting in an ADC 660, a reconstruction of the propagation constant of the waveguide unit 110 in a transmission mode and reflection mode are done in the digital domain by a reconstruction unit 670 outputting the magnitude A and the phase B of the signal.

Figure 7A:
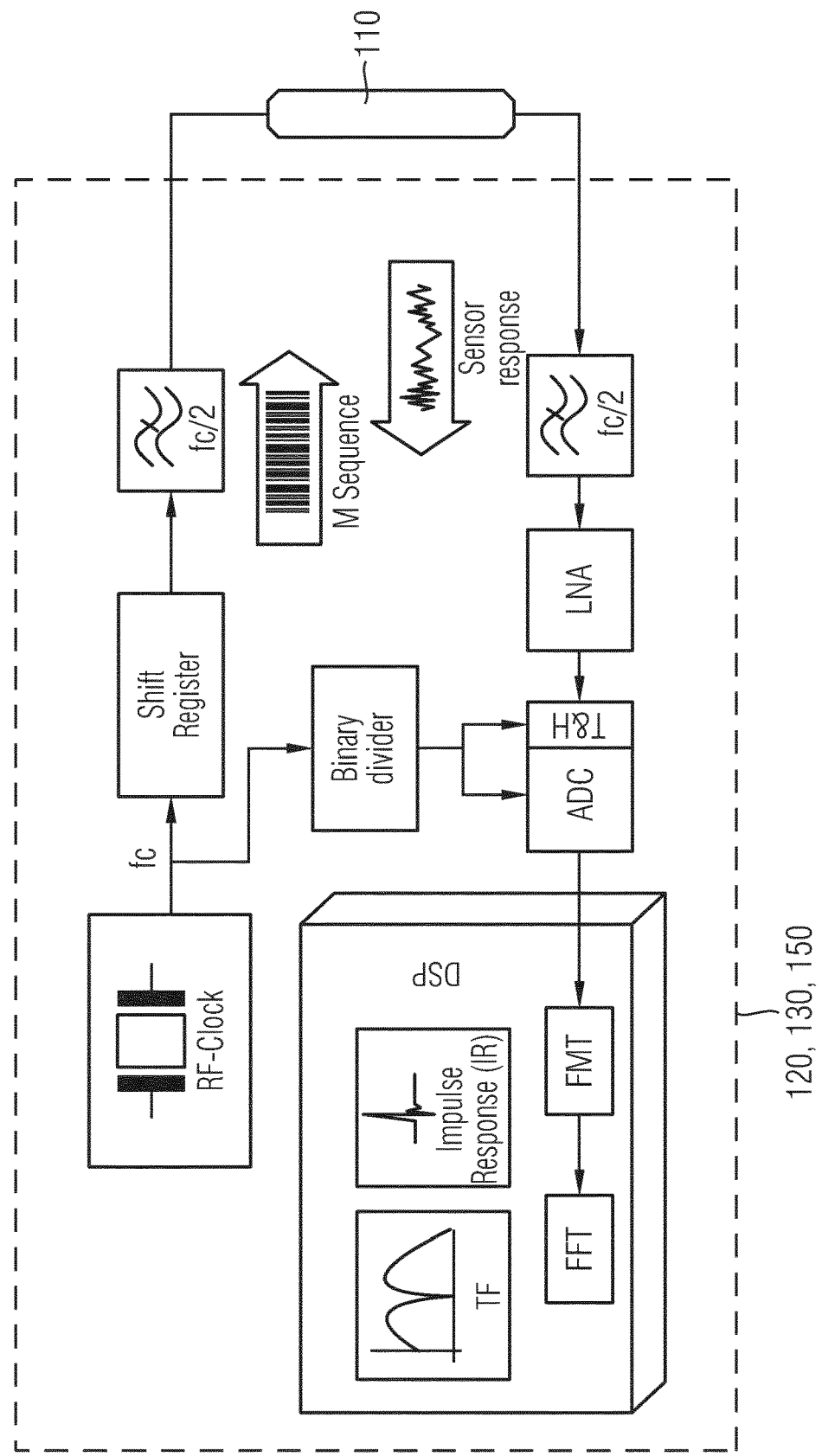
FIG. 7A is a schematic block diagram illustrating an ultra-wideband impedance spectrometer setup in a transmission mode of the electromagnetic wave sensor according to one or more embodiments.
Figure 7B:
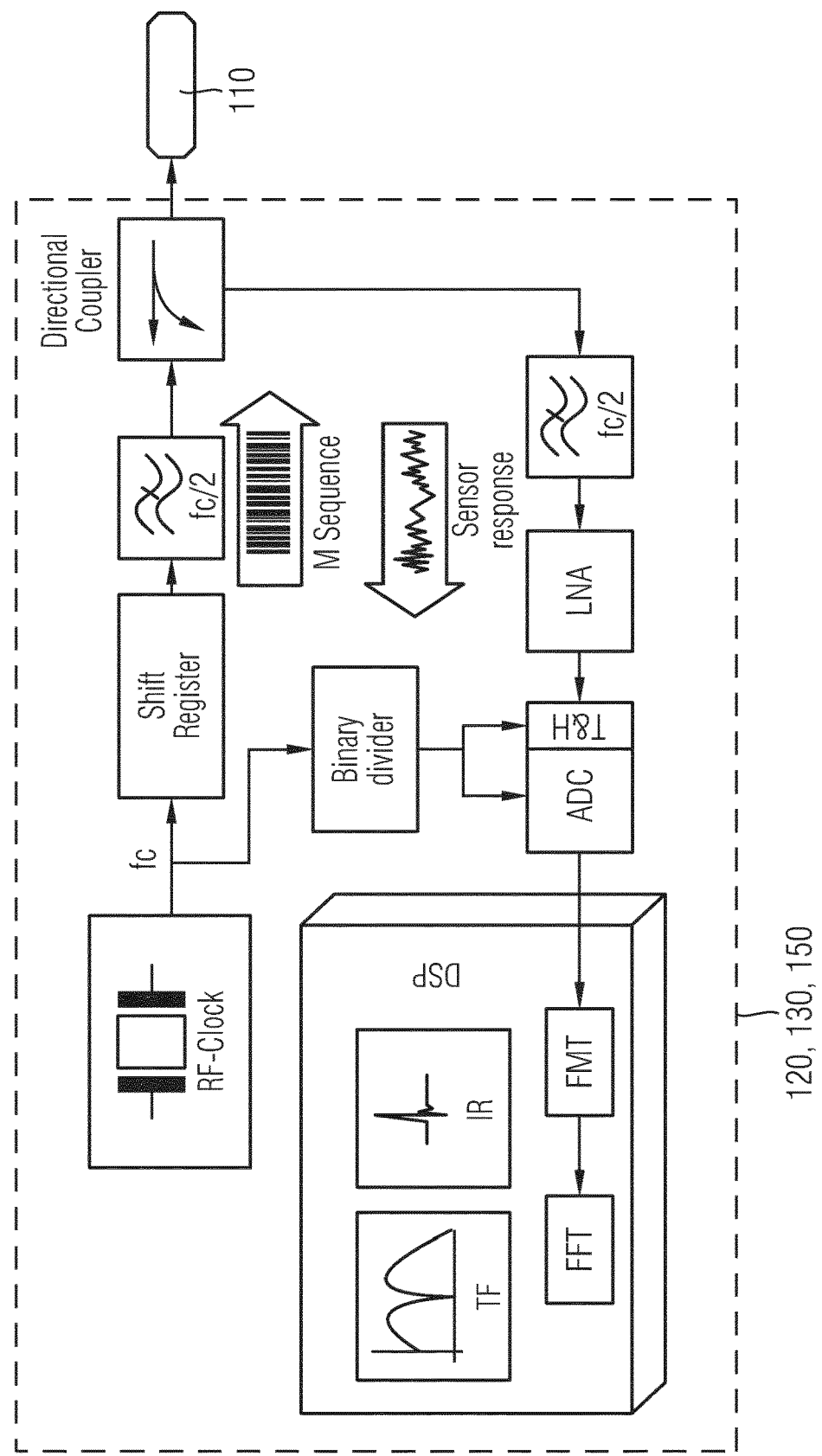
FIG. 7B is a schematic block diagram illustrating an ultra-wideband impedance spectrometer setup in a reflection mode of the electromagnetic wave sensor according to one or more embodiments.
Figure 7C:
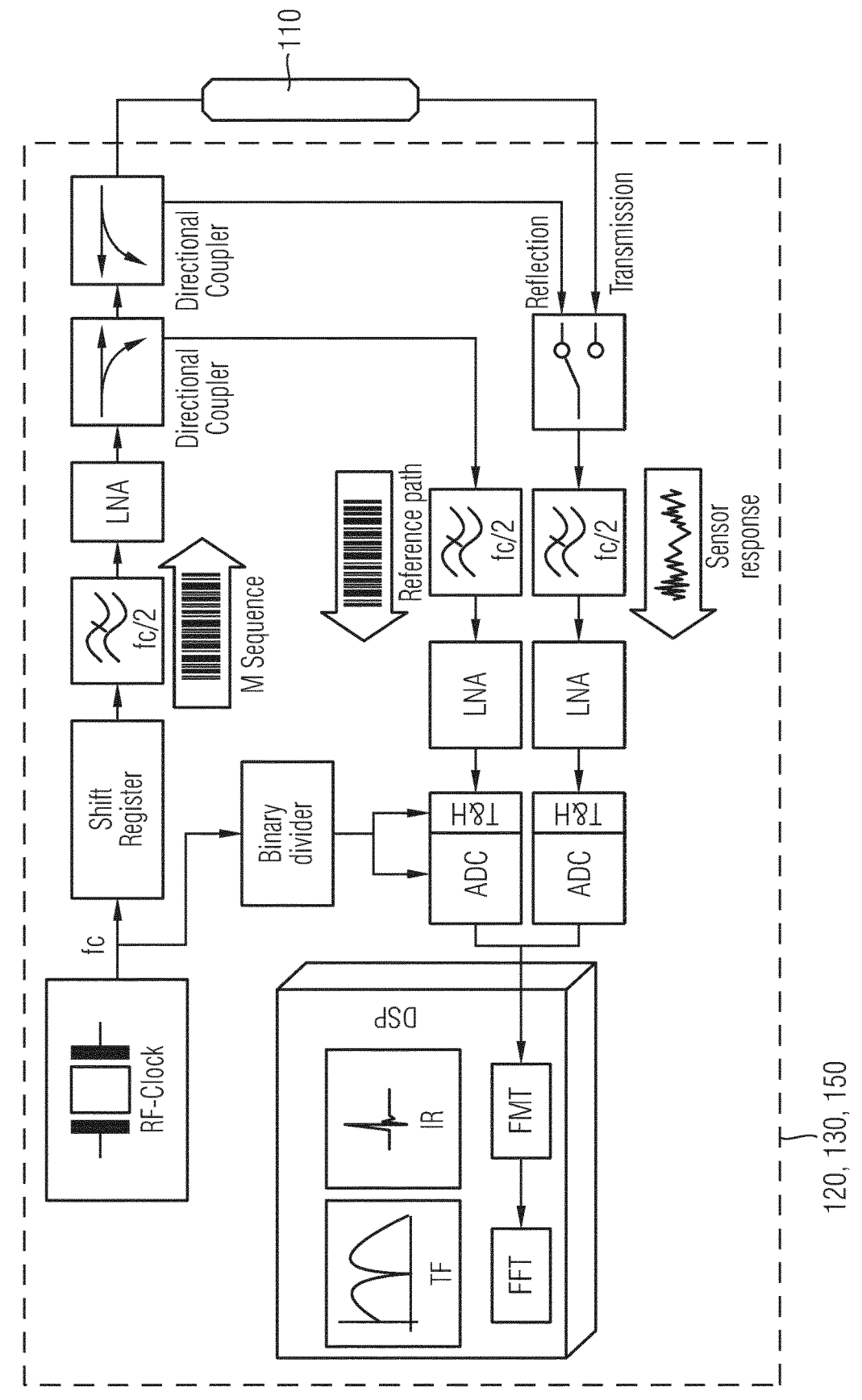
FIG. 7C is a schematic block diagram illustrating an ultra-wideband impedance spectrometer setup in a transmission and reflection mode of the electromagnetic wave sensor according to one or more embodiments.

FIGS. 7A to 7C show embodiments of an ultra-wideband impedance spectrometer according to different embodiments. In the following, a method for determining a hydration status of a body tissue 10 in vivo will be described, which is based on pseudo-random binary sequences. This method uses an ultra-wideband sequence to excite a big portion of the frequency spectrum making possible to characterize the propagation constant or transfer function of the waveguide unit 110 without the need to make a frequency sweep. By using signals like the maximal length sequences or the golden codes, it is possible to use subsampling methods, taking advantage of the periodic nature of the signals in order to use low speed analogue-to-digital converters. Once the response of the waveguide unit 110 on the transmission path or in the reflection path, the propagation constant of the waveguide unit 110 is obtained by finding the impulse response of the system through the cross correlation with the original sequence and by finding the transfer function of the system through the fast fourier transformation (FFT) of the impulse response.

According to random noise theory, the cross-correlation of an input with an output of a linear time-invariant system (LTI) under white noise excitation is proportional to a system impulse response h. From signal processing theory, the impulse response of the system in the time domain is equivalent to the transfer function of the system in the frequency domain. Therefore, the Fourier transform of the impulse response gives the transfer function (TF) of the LTI system. The random noise may be replaced with a maximum length sequence (M-sequence). Maximum length sequences are periodic sequences of integers. In the case of binary sequences, the integers are restricted to having two values only, say +1 and −1. They are generated by n-stage shift registers and the period length L is:

$$L=2^n-1 \qquad (10)$$

The M-sequences have two characteristics that are important. The first one is that the Fourier transform (FT) has the same magnitude for all frequency components (except the dc component). Thus, their power spectrum is like that of a single impulse, namely independent of frequency. It is only necessary to cross-correlate the output response of the system Y with the same M-sequence that is used for exciting the system to obtain the desired system impulse response. The normalized impulse response of the system is given by:

$$h = MY/(L+1) \tag{11}$$

In formula (11), the vectors h and Y are the vectors of L elements corresponding to the impulse response and the output response of the LTI system. M is an L×L matrix containing the right circularly delayed version of the sequence M with a period equal to L times the clock period. The computation MY can be performed efficiently by using special techniques developed in Hadamard spectroscopy. When the Hadamard transformation is applied to an M sequence, it is called fast M-sequence transformation (FMT). It provides an efficient way to derive the cross-correlation function between the M-sequence excitation signal and the output response of the system, because it consists of only additions and subtractions. The second property is concerned with the periodicity of the M-sequences. Thanks to the periodicity of the M-sequences, it is possible to subsample the output signal of the system in order to use low cost analogue to digital converters.

The properties of the M-sequence are useful to characterize linear systems and can be used in the area of the electromagnetic wave and millimetre wavelength signals to construct an ultra-wideband impedance spectrometer.

A schematic diagram of a measurement system comprising the electromagnetic wave transmitter unit 120, the electromagnetic wave receiver unit 130, the processor unit 150, and the waveguide unit 110 is illustrated in FIG. 7A. The M-sequence is generated by a fast n-stage shift register with an appropriate feedback, which is driven by an RF clock frequency L. Since nearly 80% of the signal energy is concentrated from DC to $f_c/2$, the M-sequence signal has to be low pass filtered to $f_c/2$. The filtered M-sequence is applied to the linear time invariant system to be characterized, which may be the waveguide unit 110 having an electromagnetic wave fringe field being in contact with the body tissue 10. After low pass filtering and amplification by means of a Low-Noise Amplifier LNA, the response of the system in the continuous time domain is sampled into digital form by an A/D converter ADC. The clock rate of the M-sequence will be divided by a frequency binary divider in order to drive the A/D converter ADC and a track and hold unit T&H in a subsampling mode. Within a digital signal processor DSP, the sampled response is converted into the impulse response using the FMT. Finally, a fast fourier transform (FFT) gives the transfer function (TF) of the system in the frequency domain.

With the systems comprising the electromagnetic wave transmitter unit 120, the electromagnetic wave receiver unit 130, the processor unit 150, and the waveguide unit 110 as shown in FIGS. 7A to 7C, it is possible to measure the response in transmission and in reflection of the waveguide unit 110. Herein, FIG. 7A shows a system comprising the electromagnetic wave transmitter unit 120, the electromagnetic wave receiver unit 130, the processor unit 150, and the waveguide unit 110 for transmission measurement. FIG. 7B shows a measurement system comprising the electromagnetic wave transmitter unit 120, the electromagnetic wave receiver unit 130, the processor unit 150, and the waveguide unit 110 for reflection. In comparison with the setup for measurements in transmission, the system to measure the response of this waveguide unit 110 in reflection as shown in FIG. 7B is equipped with a directional coupler that enables the measurement of the electromagnetic waves that are reflected in the electromagnetic wave guide unit 110 due to the impedance mismatch depending on composition of the body tissue 10.

As shown in FIG. 7C, a system comprising the electromagnetic wave transmitter unit 120, the electromagnetic wave receiver unit 130, the processor unit 150, and the waveguide unit 110 may also be configured to measure a response of the waveguide unit 110 in transmission and in reflection. Herein, the system additionally includes a second measurement path to record a reference signal. The reference signal can be used to calibrate changes in the sender power and in the phase. To save energy, only one additional measurement path was added. That means that it is only possible to measure either the reflection response or the transmission response at one time.

By means of the systems comprising the electromagnetic wave transmitter unit 120, the electromagnetic wave receiver unit 130, the processor unit 150, and the waveguide unit 110 as described above with regard to FIGS. 7A to 7C, a transmission or reflection spectrum of the body tissue 10 of the waveguide unit 110 having a fringe field penetrating the body tissue 10 may be measured.

Figure 8:
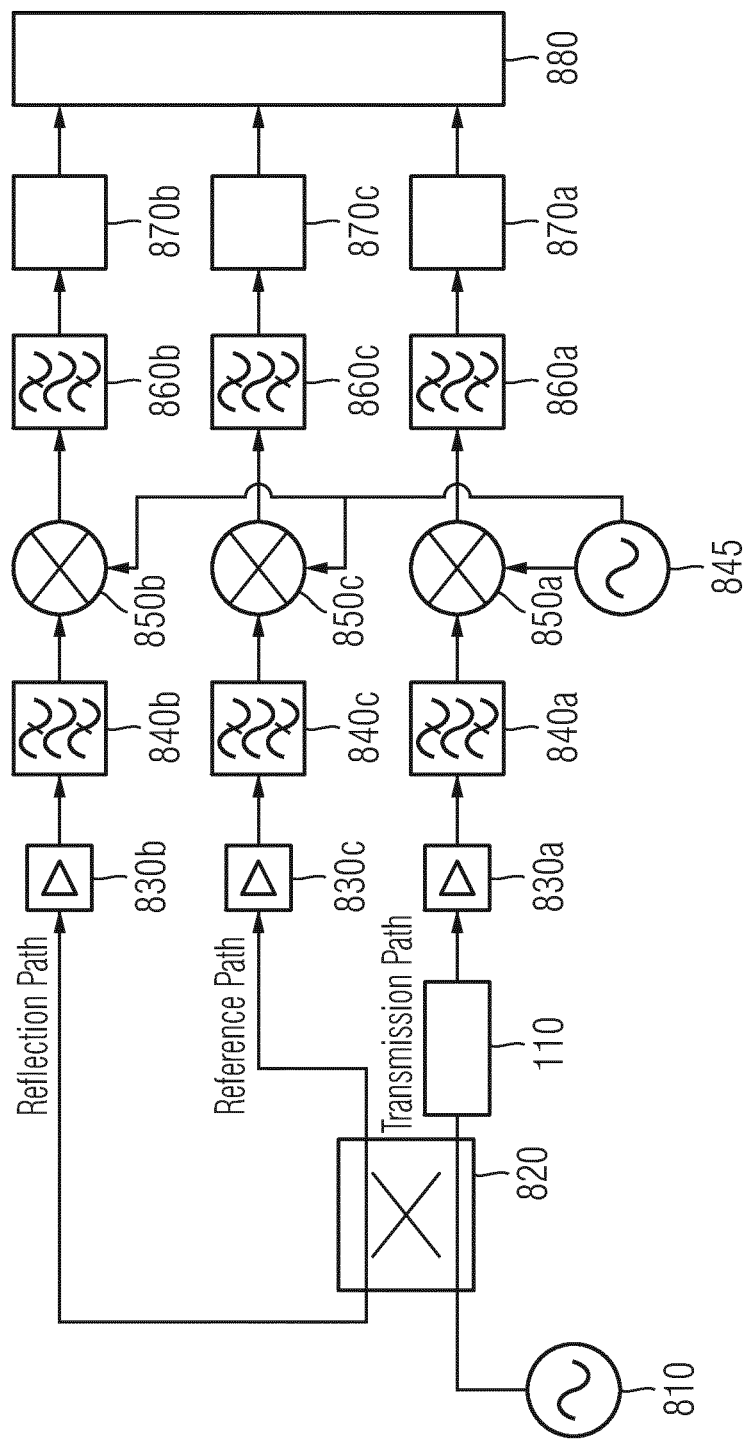
FIG. 8 is a schematic block diagram illustrating a structure of a system for a superheterodyne-based method for determining a hydration status of a body tissue in vivo according to one or more embodiments.

FIG. 8 is a schematic block diagram illustrating a structure of a system for a superheterodyne-based method for determining the hydration status in vivo. As can be seen from FIG. 8, a radio frequency source 810 and a local oscillator 845 are provided, which are adapted to make a frequency sweep between DC and 100 GHz by using frequency modulated signals. Both the radio frequency source 810 and the local oscillator 845 are locked to the same frequency reference (synchronized). The radio frequency signal is provided to the waveguide unit 110 via a directional coupler 820, wherein the signals from the transmission path, the reflection path, and the reference path are supplied to amplifiers 830a, 830b, and 830c, respectively. The signals from the amplifiers 830a, 830b, and 830c are filtered by first filters 840a, 840b, and 840c, respectively, and down converted by mixers 850a, 850b, and 850c being each connected to the local oscillator 845 and by second filters 860a, 860b, and 860c, respectively. The respective signals from the filters 860a, 860c, and 860b are converted to a digital signal by analogue to digital converters 870a, 870c, and 870b, respectively. The down conversion is performed in order to reduce the sample frequency requirements of the analogue to digital converters 870a, 870c, and 870b. Thus, effects of aliasing due to high frequencies are avoided. To calculate the propagation constant or transfer function of the transmission and the reflection path, it is necessary to demodulate the digitized channel information to baseband and reconstruct the amplitude and phase information. The reconstruction of the amplitude and phase information and the calculation of the propagation constant are executed in the digital signal processor 880.

Figure 9:
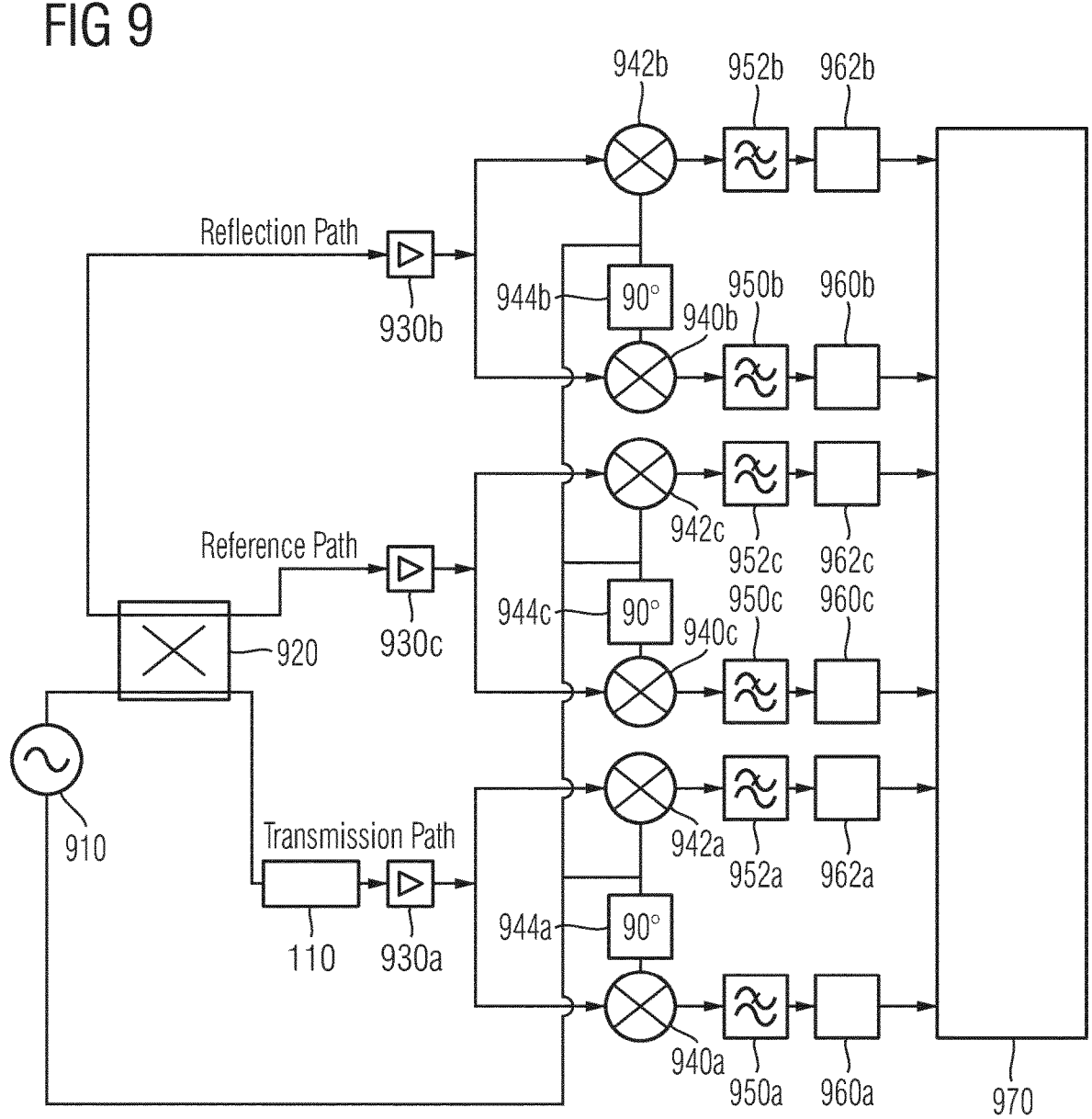
FIG. 9 is a schematic block diagram illustrating a structure of a system for a direct conversion based method for determining a hydration status of a body tissue in vivo according to one or more embodiments.

FIG. 9 is a schematic block diagram of a structure of a system for a direction conversion based method for determining a hydration status in vivo. As can be seen from FIG. 9, a radio frequency source 910 is provided, which is adapted to sweep a frequency between DC and 100 GHz. The homodyne or direct conversion method uses the radio frequency source 910 to generate a frequency-modulated signal that can cover the frequency spectrum between DC and 100 GHz by making a frequency sweep. The radio frequency signal is provided to the waveguide unit 110 via a directional coupler 920, wherein the signals from the transmission path, the reflection path, and the reference path are supplied to amplifiers 930a, 930b, and 930c, respectively. The individual signals coming from the amplifiers 930a, 930b, and 930c in the transmission path, reflection path and in the reference path, respectively, are demodulated and filtered by using an IQ demodulation method. In comparison with the superheterodyne method, the amplitude and phase information is reconstructed in the analogue domain and requires only one signal source. The signals in the transmission path, the reflection path and the reference path are split and fed into mixers 940a, 942a for the transmission path, into mixers 940b, 942b for the reflection path, and into mixers 940c, 942c for the reference path. The mixers 942a, 942b, and 942c and the mixers 940a, 940b, and 940c are each connected to the radio frequency source 910, wherein 90°-phase shifters 944a, 944b, and 944c are interconnected between the mixers 940a, 940b, and 940c and the radio frequency source 910, respectively. The signals from the mixers 940a, 942a, 940b, 942b, 940c and 942c are fed into filters 950a, 952a, 950b, 952b, 950c, 952c, respectively. The respective signals from the filters 950a, 952a, 950b, 952b, 950c, 952c are converted to a digital signal by analogue to digital converters 960a, 962a, 960b, 962b, 960c, and 962c, respectively. The calculation of the amplitude and phase information and the propagation constant are executed in the digital signal processor 970.

The electromagnetic wave sensor 100 uses the modification of the propagation characteristics between DC and 100 GHz of a transmission line to measure in a non-invasive way the hydration level of blood of a human or animal. The transmission line can be a microwave aerial, open ended transmission line or leaky transmission line. The main advantage of this method is the reduction on size of the device and the reduction of the power needed to the make the measurements besides the reduction of errors due to spurious reflections.

Herein, a change in a waveguide or in a leaky waveguide is performed to measure electrolyte concentrations and water content in life tissue. Further, microwaves are used to measure the water content and the electrolyte concentration in life tissue. In addition, ultra-wideband microwave signals are used to measure the temperature, water content and electrolyte concentration through different layers in a life tissue. Furthermore, vector network analyser like structures (homodyne architecture, heterodyne architecture, six-port architecture or pseudo-random sequence architecture) are used to measure the changes of the propagation constant (reflection or transmission or both) of a waveguide in order to determine the water content and the electrolyte content of the different life tissue layers.

Although specific embodiments have been illustrated and described herein, it will be appreciated by those of ordinary skill in the art that a variety of alternate and/or equivalent implementations may be substituted for the specific embodiments shown and described without departing from the scope of the embodiments. This application is intended to cover any adaptations or variations of the specific embodiments discussed herein. Therefore, it is intended to be limited only by the claims and the equivalents thereof.

What is claimed is:

1. An electromagnetic wave sensor for determining a hydration status of a body tissue in vivo, the electromagnetic wave sensor comprising:
    an electromagnetic wave transmitter configured to emit an electromagnetic wave signal in a frequency range between 1 Hz and 1 THz;
    a waveguide coupled to the electromagnetic wave transmitter, the waveguide being adapted to be arranged next to the body tissue such that a fringe field of the electromagnetic wave signal guided by the waveguide penetrates the body tissue;
    an electromagnetic wave receiver coupled to the waveguide and configured to receive the electromagnetic wave signal modified by the body tissue in dependence of a hydration status of the body tissue; and
    at least one processor configured to determine the hydration status of the body tissue from the electromagnetic wave signal modified by the body tissue in dependence of the hydration status of the body tissue, wherein the at least one processor is configured to determine the hydration status on a basis of a frequency analysis of a transfer function between the electromagnetic wave transmitter and the electromagnetic wave receiver.

2. The electromagnetic wave sensor according to claim 1, wherein the electromagnetic wave receiver is configured to receive the electromagnetic wave signal transmitted by the waveguide.

3. The electromagnetic wave sensor according to claim 1, wherein the electromagnetic wave receiver is configured to receive the electromagnetic wave signal reflected in the waveguide.

4. The electromagnetic wave sensor according to claim 1, wherein the waveguide is a micro strip line or a coplanar waveguide.

5. The electromagnetic wave sensor according to claim 1, wherein the electromagnetic wave transmitter is configured to emit electromagnetic wave signals in a frequency range between 1 GHz and 100 GHz.

6. The electromagnetic wave sensor according to claim 1, wherein the electromagnetic wave transmitter is configured to sweep a frequency of the electromagnetic wave signal in a frequency range having a bandwidth of at least 5 GHz, wherein, during a sweep, the electromagnetic wave transmitter continuously varies the frequency from a first frequency to a second frequency that has a difference of at least 5 GHz from the first frequency.

7. The electromagnetic wave sensor according to claim 1, wherein the electromagnetic wave transmitter is configured to emit the electromagnetic wave signal having frequency components within a frequency bandwidth of at least 5 GHz.

8. The electromagnetic wave sensor according to claim 1, wherein the at least one processor is configured to determine the hydration status on a basis of a frequency shift of a peak in the transfer function depending on the hydration status.

9. The electromagnetic wave sensor according to claim 1, further comprising:
    a graphical user interface configured to display the hydration status.

10. The electromagnetic wave sensor according to claim 1, further comprising:
    a memory unit configured to store measurement data or processed data.

11. The electromagnetic wave sensor according to claim 1, further comprising:
    a temperature sensor configured to measure the temperature of the body tissue.

12. The electromagnetic wave sensor according to claim 1, further comprising:
    an energy storage unit configured to supply energy to the electromagnetic wave sensor; and
    an energy harvesting unit configured to harvest electromagnetic wave energy from an external power source and charge the energy storage unit using the harvested electromagnetic wave energy.

13. The electromagnetic wave sensor according to claim 1, further comprising:
a communication unit configured to transmit data related to the electromagnetic wave signal modified by the body tissue in dependence of the hydration status of the body tissue to an external device.

14. A system for determining a hydration status of a body tissue in vivo, the system comprising:
an electromagnetic wave sensor comprising:
an electromagnetic wave transmitter configured to emit an electromagnetic wave signal in a frequency range between 1 Hz and 1 THz;
a waveguide coupled to the electromagnetic wave transmitter, the waveguide being adapted to be arranged next to the body tissue such that a fringe field of the electromagnetic wave signal guided by the waveguide penetrates the body tissue;
an electromagnetic wave receiver coupled to the waveguide and configured to receive the electromagnetic wave signal modified by the body tissue in dependence of a hydration status of the body tissue;
a communication unit configured to transmit data related to the electromagnetic wave signal modified by the body tissue in dependence of the hydration status of the body tissue; and
at least one processor configured to determine the hydration status of the body tissue from the electromagnetic wave signal modified by the body tissue in dependence of the hydration status of the body tissue, wherein the at least one processor is configured to determine the hydration status on a basis of a frequency analysis of a transfer function between the electromagnetic wave transmitter and the electromagnetic wave receiver; and
an external device configured to receive the data from the communication unit of the electromagnetic wave sensor.

15. The system according to claim 14, wherein the external device is a mobile device fixed to an armband or to a belt, a cellular phone, a smart phone, a personal computer, a tablet personal computer, a wrist watch, a smart watch, glasses, or a bedside device.

16. The system according to claim 14, wherein the communication unit, the electromagnetic wave transmitter, and the electromagnetic wave receiver are integrated in a monolithic circuit, the electromagnetic wave transmitter and the electromagnetic wave receiver being connected to the waveguide, wherein the waveguide is integrated in a skin patch.

\* \* \* \* \*